(12) United States Patent
Pesala

(10) Patent No.: US 12,343,179 B2
(45) Date of Patent: Jul. 1, 2025

(54) DIGITAL KIOSK FOR PERFORMING INTEGRATIVE ANALYSIS OF HEALTH AND DISEASE CONDITION AND METHOD THEREOF

(71) Applicant: AYUR.AI PRIVATE LIMITED, Chennai (IN)

(72) Inventor: Balasubrahmanyam Pesala, Chennai (IN)

(73) Assignee: AYUR.AI PRIVATE LIMITED, Chennai (IN)

( * ) Notice: Subject to any disclaimer, the term of this patent is extended or adjusted under 35 U.S.C. 154(b) by 0 days.

(21) Appl. No.: 18/407,743

(22) Filed: Jan. 9, 2024

(65) Prior Publication Data

US 2024/0138780 A1    May 2, 2024

Related U.S. Application Data

(63) Continuation of application No. PCT/IB2022/056266, filed on Jul. 7, 2022.

(30) Foreign Application Priority Data

Jul. 9, 2021 (IN) .............................. 202141030804

(51) Int. Cl.
*A61B 5/00* (2006.01)
*A61B 5/0205* (2006.01)
(Continued)

(52) U.S. Cl.
CPC .......... *A61B 5/7445* (2013.01); *A61B 5/0205* (2013.01); *A61B 5/4854* (2013.01);
(Continued)

(58) Field of Classification Search
CPC ... A61B 5/7445; A61B 5/0205; A61B 5/4854; A61B 5/7267; A61B 5/0077;
(Continued)

(56) References Cited

U.S. PATENT DOCUMENTS 10,699,206 B2    6/2020  Tiexeira
10,943,407 B1 *  3/2021  Morgan ................. G16H 15/00
(Continued)

FOREIGN PATENT DOCUMENTS

CN    111292821 A    6/2020

OTHER PUBLICATIONS

International Search Report for PCT/IB2022/056266, dated Nov. 16, 2022, 3 pages.
(Continued)

*Primary Examiner* — Joseph M Dietrich
*Assistant Examiner* — Michael T. Holtzclaw
(74) *Attorney, Agent, or Firm* — Cozen O'Connor

(57) ABSTRACT

A digital kiosk for performing integrative analysis of health and disease condition and method thereof is disclosed. The digital kiosk (100) comprises a three-dimensional image capturing system configured for capturing phenotypic features associated with a patient using one or more computer vision-based models. The digital kiosk (100) further comprises one or more health sensors (102) configured for capturing physiological health signals associated with the patient, a user interface for obtaining one or more user inputs from the patient, a communication module for establishing communication session with one or more external devices (106), a hardware processor (208) and a memory (202) coupled to the hardware processor (208). The memory (202) comprises a set of program instructions in the form of plurality of subsystems (200) configured to be executed by the hardware processor (208). The plurality of subsystems (200) comprises a medical input data collection subsystem (210), a health status computation subsystem (212) and a disease identification subsystem (214).

15 Claims, 29 Drawing Sheets

(51) Int. Cl.
  *G16H 10/60* (2018.01)
  *G16H 50/20* (2018.01)
  *G16H 50/30* (2018.01)
  *G16H 70/60* (2018.01)
(52) U.S. Cl.
  CPC .......... *A61B 5/7267* (2013.01); *A61B 5/7275* (2013.01); *G16H 10/60* (2018.01); *G16H 50/20* (2018.01); *G16H 50/30* (2018.01); *G16H 70/60* (2018.01); *A61B 5/0077* (2013.01)
(58) Field of Classification Search
  CPC ........ G16H 70/60; G16H 50/20; G16H 50/30; G06N 5/045; G06N 3/042; G06N 20/00
  USPC .................................................. 600/300–301
  See application file for complete search history.

(56) References Cited

U.S. PATENT DOCUMENTS

| 2014/0073969 | A1* | 3/2014  | Zou ........................ A61B 5/346 |
|              |     |         | 600/479                                  |
| 2017/0249434 | A1  | 8/2017  | Brunner                                  |
| 2017/0308671 | A1  | 10/2017 | Bahrami et al.                           |
| 2020/0312455 | A1  | 10/2020 | Bhalotia                                 |
| 2020/0365275 | A1* | 11/2020 | Barnett ................ A61B 5/4803     |
| 2021/0090738 | A1  | 3/2021  | Bates                                    |

OTHER PUBLICATIONS

Written Opinion for PCT/IB2022/056266, dated Nov. 16, 2022, 6 pages.
EP Search Report mailed Sep. 25, 2024, in EP App No. 22837137, 1 page.

* cited by examiner

| Reference/ Prediction | VP | PK | VK |
|---|---|---|---|
| VP | 162 | 0 | 0 |
| PK | 3 | 19 | 4 |
| VK | 16 | 9 | 10 |

DIGITAL KIOSK FOR PERFORMING INTEGRATIVE ANALYSIS OF HEALTH AND DISEASE CONDITION AND METHOD THEREOF

EARLIEST PRIORITY DATE

This application claims priority from a Provisional patent application filed in India having patent application No. 202141030804, filed on Jul. 9, 2021, and titled "SYSTEM AND METHOD FOR INTEGRATIVE COMBINATION OF TRADITIONAL SCIENCE WITH MODERN METHODS FOR PERSONALIZED HEALTH, WELLNESS AND MEDICINE".

FIELD OF INVENTION

Embodiments of the present disclosure relates to medical diagnosis systems, and more particularly to a digital kiosk for performing integrative analysis of health and disease condition and method thereof.

BACKGROUND

Currently, ancient medical system such as Ayurveda is developing to promote an integrative and healthy lifestyle. However, a highly subjective nature of diagnosis by an Ayurveda doctor makes a process inaccurate and is not easily interpretable. The Ayurveda has a great potential for personalized, preventive, predictive, participatory, and pro-motive (P5) medicine. Ayurveda practice requires a baseline estimation (prakriti estimation) of an individual followed by differential diagnosis of disease (vikriti estimation). Current methods of the prakriti and the vikriti estimation requires deep expertise and these current methods are time consuming. Hence, quantitative, evidence-based methods are need of an hour. The Ayurveda has significant potential for personalized and preventive medicine. Currently, Ayurveda diagnosis is qualitative and requires deep expertise. Improper diagnosis may lead to sub-optimal patient outcomes. Hence, there is a need to develop quantifiable devices integrated with data driven frameworks for rapid, accurate diagnosis as per Ayurveda principles. Additionally, the qualifiable devices may also provide personalized and holistic health, wellness, and diseases recommendation. Finally, the Ayurveda doctors may also require continuous quantifiable feedback to assess efficacy of a treatment.

Currently, several companies provide Ayurveda diagnostic and teleconsulting services. However, solutions of these companies do not provide a digital Artificial Intelligence (AI) assist for the Ayurveda doctors for accurate diagnosis and therapeutics. There have been several attempts to develop electronic devices based on pressure sensors, electrocardiogram (ECG), and the like for determination of the Vikriti using pulse diagnosis methods. However, these electronic devices show the aggravation of dosha which is Vata dosha, Pitta dosha, and Kapha dosha and these electronic devices do not exactly diagnose a disease. Additionally, unlike a modern doctor who is typically specialized in a few sets of diseases, the Ayurveda doctors are required to diagnose hundreds of diseases. Further, each modern disease has several sub-types described in the Ayurveda. For example, diabetes has more than fifteen sub-types described in the Ayurveda with various clinical manifestations. Therefore, the Ayurveda doctor may have to diagnose the disease accurately including the sub-type. Additionally, treatment options for curing the disease may have to be highly personalized. Finally, the Ayurveda doctor may have to monitor therapeutic efficiency continuously by monitoring the disease symptoms and pulse parameters. This is needed to fine-tune the treatment. Therefore, effective digital solutions are required for quantifiable Ayurveda assessment and other traditional system-based patient assessment and patient specific personalized recommendations.

Hence, there is a need for an improved digital kiosk for performing integrative analysis of health and disease condition and method thereof to address the aforementioned issue.

BRIEF DESCRIPTION

In accordance with one embodiment of the disclosure, a digital kiosk for performing integrative analysis of health and disease condition of a patient using AI based traditional data and modern data network is disclosed. The digital kiosk comprises a three-dimensional image capturing system configured for capturing phenotypic features associated with a patient using one or more computer vision-based models. The digital kiosk further comprises a one or more health sensors configured for capturing physiological health signals associated with the patient. The digital kiosk further comprises a user interface for obtaining one or more user inputs from the patient. The digital kiosk further comprises a communication module for establishing communication session with one or more external devices. The digital kiosk further comprises a hardware processor and a memory coupled to the hardware processor. The memory comprises a set of program instructions in the form of plurality of subsystems configured to be executed by the hardware processor. The plurality of subsystems comprises a medical input data collection subsystem configured to collect patient information and the phenotypic features associated with the patient from a plurality of medical devices, computer vision-based models, and a conversational artificial intelligence questionnaire, and one or more inputs from digital biomarkers and modern markers such as biochemical markers, genomic markers, and multi-omics markers. The phenotypic features comprise anatomic features, physical, physiological features, psychological features of the patient. The medical input data collection subsystem is further configured to collect blood pulse parameters from the captured physiological health signals for ayurveda or traditional medicine diagnosis from the one or more health sensors. The ayurveda or the traditional medicine diagnosis uses pulse rate, pulse rate variability, pulse pressure, pulse transit time, and pulse morphology. Throughout the specification, the AI questionnaire may also be referred as conversational artificial intelligence questionnaire, set of questionnaires, conversational artificial intelligence questionnaire based adaptive questionnaire and the like.

The plurality of subsystems further comprises a health status computation subsystem configured to apply the collected patient information, the captured phenotypic features, the one or more inputs and the blood pulse parameters associated with the patient on to a trained machine learning model and predict real time set of traditional medicine system parameters based on the results of the trained machine learning model.

The plurality of subsystems further comprises a disease identification subsystem configured to compare the real time set of traditional medicine system parameters with pre-stored real time set of traditional medicine system parameters, identify a disease based on the compared results and based on pre-stored disease database, generate a recommendation message to the patient based on the identified disease and the like.

The recommendation message comprises health and disease condition of the patient, health parameters, therapeutic interventions, clinical interventions, one or more medical remedies, and treatment plan. The disease identification subsystem is further configured to perform one or more operations based on the generated recommendation message and the patient prior approval. The one or more operations comprises generating alerts for the patient representatives, generating alerts for medical representatives, generating new treatment plan and generating new diet plan. The disease identification subsystem is further configured to output the generated recommendation message and the one or more operations on the user interface.

Embodiment of another disclosure comprises a method for performing an integrative analysis of health and disease condition of the patient using AI based traditional data and the modern data network. The method comprises capturing phenotypic features associated with the patient using one or more computer vision-based models by an image capturing system.

The method further comprises capturing physiological health signals associated with the patient by one or more health sensors.

The method further comprises collecting patient information and the phenotypic features associated with the patient from a plurality of medical devices, computer vision-based models, and a conversational artificial intelligence questionnaire, and one or more inputs from digital biomarkers, clinical markers, biochemical markers, genomic markers, and multi-omics markers. The phenotypic features comprise anatomic features, physical, physiological features, psychological features of the patient.

The method further comprises collecting blood pulse parameters from the captured physiological health signals for ayurveda or traditional medicine system diagnosis from the one or health more sensors. The ayurveda or traditional medicine system diagnosis uses pulse rate, pulse rate variability, pulse pressure, pulse transit time, and pulse morphology.

The method further comprises applying the collected patient information, the captured the phenotypic features, the one or more inputs and the blood pulse parameters associated with the patient on to a trained machine learning model.

The method further comprises predicting real time set of traditional medicine system parameters based on the results of the trained machine learning model.

The method further comprises comparing the real time set of traditional medicine system parameters with pre-stored real time set of traditional medicine system parameters.

The method further comprises identifying a disease based on the compared results and based on pre-stored disease database.

The method further comprises generating a recommendation message to the patient based on the identified disease. The recommendation message comprises of health and disease condition of the patient, health parameters, therapeutic interventions, clinical interventions, one or more medical remedies, and treatment plan.

The method further comprises performing one or more operations based on the generated recommendation message and the patient prior approval. The one or more operations comprises generating alerts for the patient representatives, generating alerts for medical representatives, generating new treatment plan, and generating new diet plan.

The method further comprises outputting the generated recommendation message and the one or more operations on the user interface.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which:

FIGS. 14A-C are graphical user interface of conversational artificial intelligence based adaptive questionnaire framework designed as per Ayurveda principles for assessing Prakriti baseline of a person, in accordance with an embodiment of the present disclosure;

FIGS. 17A-I are various screenshot representations depicting an exemplary process of a disease and health condition prediction, in accordance with an embodiment of the present disclosure.

Figure 1:
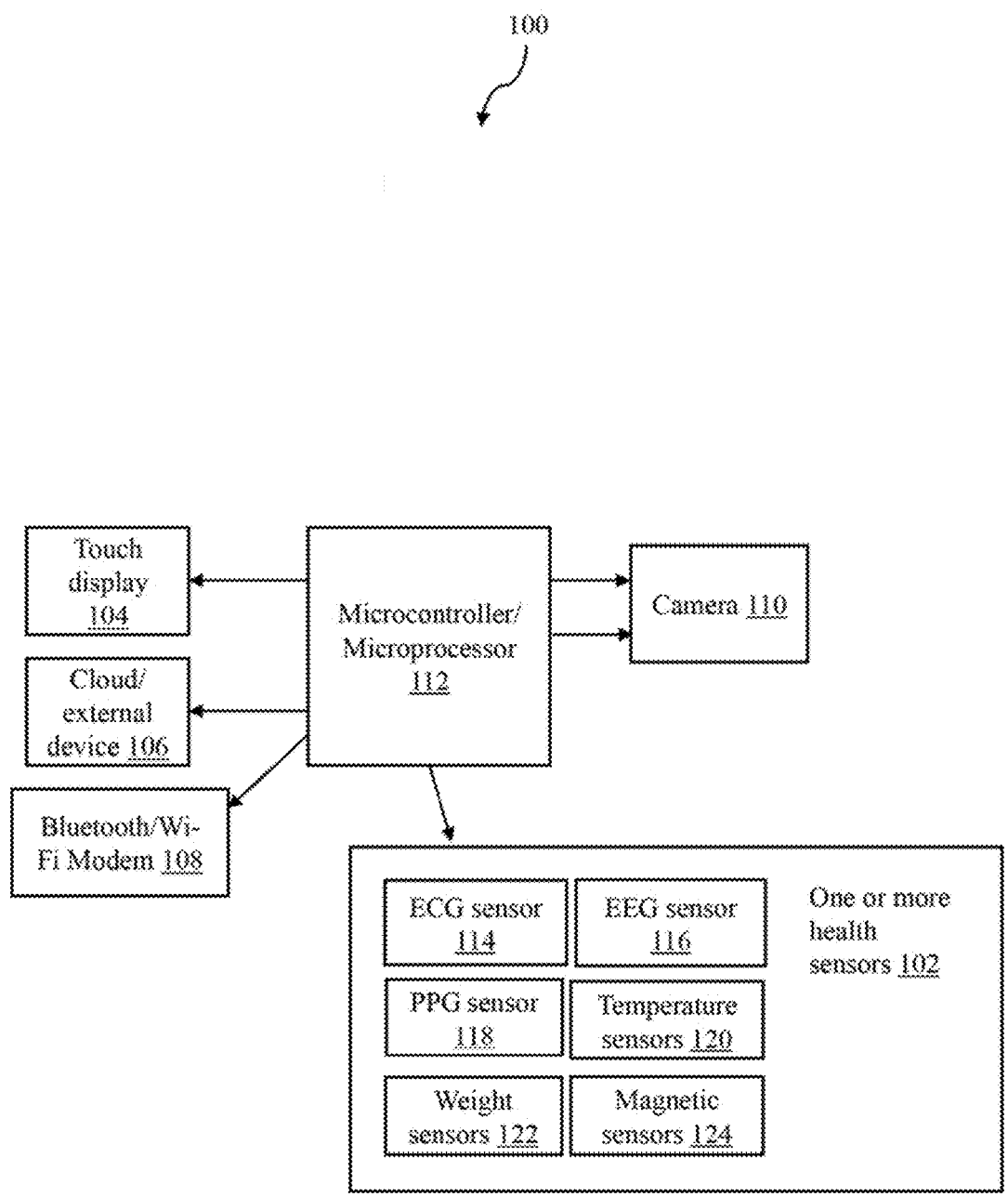
FIG. 1 is a block diagram depicting an overview of a digital kiosk, in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated online platform, and such further applications of the principles of the disclosure as would normally occur to those skilled in the art are to be construed as being within the scope of the present disclosure.

The terms "comprises". "comprising", or any other variations thereof, are intended to cover a non-exclusive inclusion, such that a process or method that comprises a list of steps does not include only those steps but may include other steps not expressly listed or inherent to such a process or method. Similarly, one or more devices or subsystems or elements or structures or components preceded by "comprises . . . a" does not, without more constraints, preclude the existence of other devices, subsystems, elements, structures, components, additional devices, additional subsystems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

A computer system (standalone, client or server computer system) configured by an application may constitute a "subsystem" that is configured and operated to perform certain operations. In one embodiment, the "subsystem" may be implemented mechanically or electronically, so a subsystem may comprise dedicated circuitry or logic that is permanently configured (within a special-purpose processor) to perform certain operations. In another embodiment, a "subsystem" may also comprise programmable logic or circuitry (as encompassed within a general-purpose processor or other programmable processor) that is temporarily configured by software to perform certain operations.

Accordingly, the term "subsystem" should be understood to encompass a tangible entity, be that an entity that is physically constructed permanently configured (hardwired) or temporarily configured (programmed) to operate in a certain manner and/or to perform certain operations described herein.

Referring now to the drawings, and more particularly to FIGS. 1 through 17, where similar reference characters denote corresponding features consistently throughout the figures, there are shown preferred embodiments and these embodiments are described in the context of the following exemplary system and/or method.

Embodiments of the present disclosure related to a digital kiosk for performing integrative analysis of health and disease condition and method thereof. The digital kiosk is integrated with an Ayurveda prakriti (baseline health) questionnaire using conversational Artificial Intelligence (AI) and a three-dimensional (3D) image capturing system. The conversational Artificial Intelligence (AI) and the three-dimensional (3D) image capturing system is integrated with advanced computer vision techniques for capturing anatomical features such as a body or a face shape, length, breadth, symmetry features, skin type, eye colour and the like for a baseline estimation. Subsequently, a vikriti (disease state) is assessed through one or more health sensors. The one or more health sensors is integrated with the digital kiosk which may perform digital pulse diagnosis. Additionally, various vision and health sensors may be used to perform accurate vikriti assessment using facial, eye, tongue, and other body parts diagnosis. A person's holistic assessment is performed objectively using machine learning and deep learning techniques. An inbuilt recommendation engine provides therapeutic guidance to Ayurveda doctors. Throughout the specification the person may also be referred as a patient, a user, an individual and the like. The health or the disease condition of the person may be defined as a state of health of the person. For example, the health or the disease condition of the person may not be good if the person is diagnosed with any physical or mental illness such as a heart disease, depression. Alzheimer's, mobility diseases and the like. Further, the health or the disease condition of the person may not be good if the person is diagnosed with a chronic illness such as heart failure, diabetes and the like which may not have any effective cure. Further, the disease condition may also indicate the criticality level of disease diagnosed in the person. For example, the disease condition may be recovering, no improvement or deteriorating or the like based on criticality level of the disease. The health condition may be healthy, weak, or risky or the like. Throughout the document the person may also be referred as patient.

The digital kiosk is integrated with a software application which may use advanced Artificial Intelligence (AI) tools. These advanced AI tools may assist the Ayurveda doctors in accurate patient assessment, diagnosis, and therapeutic recommendations.

Information from various modern biochemical markers and advanced genomic markers may be integrated for accurate vikriti assessment and for fine-tuning Ayurveda medicine, diet, meditation, Vedic chanting, music recommendations and panchakarma recommendations.

The digital kiosk uses a computer vision and one or more health sensors for accurate prakriti and vikriti estimation. A conversational AI based prakriti estimation (also referred as prakriti estimation) based on adaptive questionnaire is used which significantly reduces time of Ayurveda assessment by two-three folds. Additionally, the machine learning and deep learning techniques are used for accurate disease diagnosis including disease sub-types, using symptom-disease association questionnaire, and combining these inputs with digital pulse diagnosis. Finally, the digital kiosk is integrated with an AI driven recommendation engine. The AI driven recommendation engine provides personalized Ayurveda drugs, food, yoga, meditation, and the music recommendations. Additionally, the patient may remotely collect a symptom and pulse diagnosis data which may aid the Ayurveda doctors in continuous assessment of a therapeutic efficacy and to fine-tune recommendations to effectively cure the diseases.

The digital kiosk uses a microcontroller, processor, or a system on module such as SC66 using a Qualcomm snapdragon processor. The digital kiosk is attached with the one or more image capturing systems that captures Red, Green, Blue (RGB) and depth image to capture phenotypic features. The one or more health sensors such as ECG sensor, EEG sensor and PPG sensor captures physiological signals. A software program is developed to capture a phenotypic questionnaire and a symptom questionnaire. A prakriti (baseline) framework is validated on greater than five hundred subjects showing greater than ninety percent accuracy. A vikriti (disease) framework uses a network approach containing greater than thousand diseases and greater than six thousand symptoms which triages the disease based on the patient symptoms. The digital kiosk is subsequently designed using AutoCAD. A prototype version of the digital kiosk is realized integrating all hardware and peripherals and tested in a lab scale.

FIG. 1 is a block diagram depicting an overview of a digital kiosk 100, in accordance with an embodiment of the present disclosure. The digital kiosk 100 comprises one or more health sensors 102, a touch display 104, a cloud or one or more external devices 106, a Bluetooth or a Wi-Fi or a cellular Modem 108, a camera such as an RGB camera or a three-dimensional (3D) RGB-depth camera 110 which captures the RGB and the depth image, a microcontroller or microprocessor 112, display serial interface (DSI) pins, camera serial interface (CSI) pins, I2C control bus, I2C/serial peripheral interface (SPI) and the like. The one or more health sensors 102 are electrocardiogram (ECG) sensor 114, electroencephalogram (EEG) sensor 116, photoplethysmography (PPG) sensor 118, a temperature sensor 120, a weight sensor 122, a magnetic sensor 124 and the like. The one or more health sensors 102 is configured to capture one or more patient health parameters. The touch display 104 helps in viewing collected patient information, captured one or more patient health parameters and recommendation messages. The Bluetooth or the Wi-Fi or the cellular modem 108 helps in transmitting the collected patient information, the captured one or more patient health parameters and the recommendation messages to the one or more external devices 106 or cloud. In such an embodiment, the one or more external device 106 or the cloud enables storage, analysis, and display of the collected patient information, the captured one or more patient health parameters and the recommendation messages. The 3D RGB-depth camera 110 may be a three-dimensional image capturing system. A hardware processor, as used herein, means any type of computational circuit, such as, but not limited to, the microprocessor 112, a microcontroller, a complex instruction set computing microprocessor, a reduced instruction set computing microprocessor, a very long instruction word microprocessor, an explicitly parallel instruction computing microprocessor, a digital signal processor, or any other type of processing circuit, or a combination thereof. In one embodiment, all adjoining above-described wearable device parts are coupled with the hardware processor such as microprocessor for further analysis of data. The DSI pins are present from a touch panel and a Mobile Industry Processor Interface (MIPI) display connector. The CSI pins are present from a dual camera MIPI multi lane interface. Throughout the specification, the AI questionnaire may also be referred as conversational artificial intelligence questionnaire, set of questionnaires, conversational artificial intelligence questionnaire based adaptive questionnaire and the like. Further, throughout the specification the person may also be referred as a patient, a user, an individual and the like.

Figure 2:
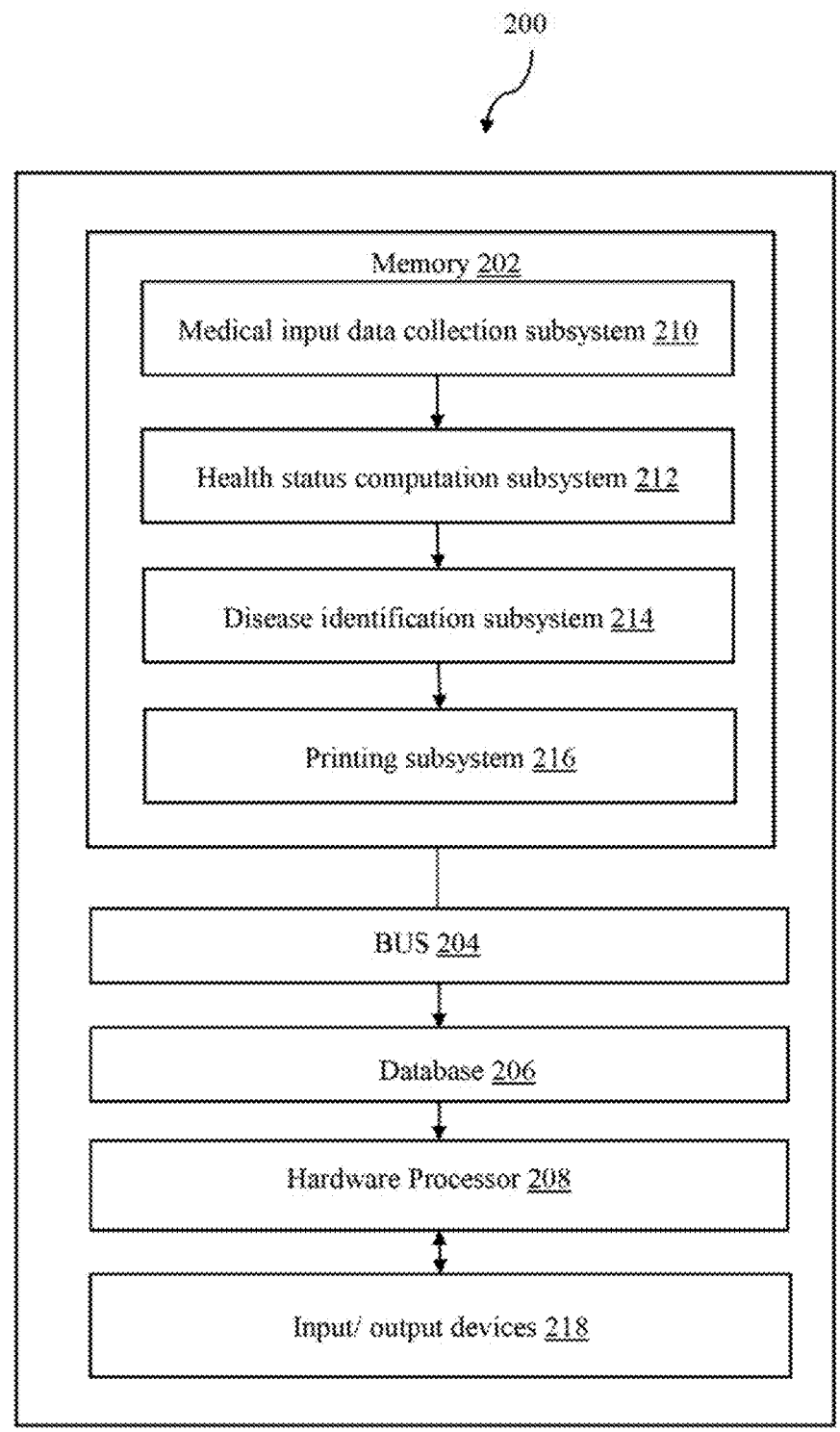
FIG. 2 is a block diagram of a digital kiosk depicting plurality of subsystems, in accordance with an embodiment of the present disclosure.

FIG. 2 is a block diagram of a digital kiosk 100 depicting plurality of subsystems 200, in accordance with an embodiment of the present disclosure.

The digital kiosk 100 comprises a three-dimensional image capturing system configured for capturing phenotypic features associated with a patient using one or more computer vision-based models. The digital kiosk 100 further comprises one or more health sensors 102 configured for capturing physiological health signals associated with the patient. The digital kiosk 100 further comprises a user interface for obtaining one or more user inputs from the patient. The digital kiosk 100 further comprises a communication module for establishing communication session with one or more external devices 106. The digital kiosk 100 further comprises a hardware processor 208 and a memory 202 coupled to the hardware processor 208.

The hardware processor(s) 208, as used herein, means any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a digital signal processor, or any other type of processing circuit, or a combination thereof.

The memory 202 includes the plurality of subsystems 200 stored in the form of executable program which instructs the hardware processor 208 via bus 204 to perform the method steps. The bus 204 enables communication between all the memory 202, the hardware processor 208 and database 206. Input/output (I/O) devices 218 (including but not limited to keyboards, displays, pointing devices, etc.) can be coupled to the system either directly or through intervening I/O controllers.

Computer memory elements may include any suitable memory device(s) for storing data and executable program, such as read only memory, random access memory, erasable programmable read only memory, electrically erasable programmable read only memory, hard drive, removable media drive for handling memory cards and the like. Embodiments of the present subject matter may be implemented in conjunction with program modules, including functions, procedures, data structures, and application programs, for performing tasks, or defining abstract data types or low-level hardware contexts. Executable program stored on any of the above-mentioned storage media may be executable by the hardware processor(s) 208.

The one or more health sensors 102 comprises a magnetic sensor 124, a photoplethysmography (PPG)) sensor 118, an electrocardiogram (ECG) sensor 114 and an electroencephalogram (EEG) sensor 116, a temperature sensor 120, and a weight sensor 122. The phenotypic feature comprises digital markers extracted from pulse electrocardiogram (ECG) data, photo plethysmograph (PPG) data, electroencephalogram (EEG) data, bioimpedance sensor data, galvanic skin response data, multispectral reflectance data, transmittance data, and autofluorescence data from plurality of body parts, sleep activity data, physical activity data and mental activity data. The three-dimensional image capturing system is further configured to capture one or more images of the patient, pre-process the one or more images to extract the phenotypic features of the patient using the computer vision-based models and transmit the extracted phenotypic features to a medical input data collection subsystem 210. The user interface is further configured to display the conversational artificial intelligence questionnaire to the patient and receive one or more responses to the conversational artificial intelligence questionnaire from the patient. The conversational artificial intelligence questionnaire is generated in real-time based on the patient information and patient responses to the conversational artificial intelligence questionnaire. The communication module is further configured to transmit the one or more operations to the one or more external devices 106 and receive responses to the transmitted one or more operations from the one or more external devices 106. The computer vision-based models may extract an uploaded one or more inputs such as the phenotypic features and returns pre-learned labels. The physiological health signals are heat, electrical impulse from muscle, brain and the like, blood volume pulse (BVP), electrocardiogram (ECG), and skin conductance level (SCL). The one or more user inputs are name of the patient, age of the patient, past health record of the patient, radiology reports, blood reports and the like. The one or more external devices 106 may be a mobile device, a laptop, a tablet, and the like. In an embodiment, for example, the three-dimensional image capturing system may be a three-dimensional (3D) RGB-depth camera 110.

The plurality of subsystems 200 comprises the medical input data collection subsystem 210, a health status computation subsystem 212, a disease identification subsystem 214 and the like.

The medical input data collection subsystem 210 is configured to collect patient information and the phenotypic features associated with the patient from a plurality of medical devices, computer vision-based models, and a conversational artificial intelligence (AI) questionnaire, and one or more inputs from digital biomarkers and modern markers such as clinical markers, biochemical markers, genomic markers, and multi-omics markers. The phenotypic features comprise anatomic features, physical, physiological features, psychological features of the patient. The medical input data collection subsystem 210 is further configured to collect blood pulse parameters from the captured physiological health signals for ayurveda or traditional diagnosis from the one or more health sensors 102. The ayurveda or the traditional diagnosis uses pulse rate, pulse rate variability, pulse pressure, pulse transit time, and pulse morphology. The digital biomarkers are defined as objective, quantifiable physiological and behavioural data of the patient.

The patient information may be patient's blood pressure, patient's heart rate, detailed picture of internal body structure of the patient, movement of patient's internal organs, family history of the patient and the like. The plurality of medical devices are pacemakers, ventilators, X-ray machines, ultrasound machines and the like. The conversational AI questionnaire may have both text and voice format and may also have multilingual support. The conversational AI questionnaire includes genetic history of various diseases in the family, death due to heart attacks, behaviour inputs such as type of food eaten, increase in weight over the years, exercise frequency and clinical symptoms such as pain in the chest, dizziness after exercise, and the like. The biochemical markers may be lipid content in the blood of the patient, inflammatory markers such as IL6, TNF-$\alpha$, alkaline phosphatase content in the patient and the like. Further, the clinical markers include those extracted from Ultrasound, X-ray, CT, angiogram, MRI, and the like. The genomic markers may be single nucleotide polymorphisms (SNPs), short tandem repeats (STRs) and indels. The multi-omics markers include genome, exome, transcriptome, metabolome, epigenome, microbiome, proteome, glycome, and the like obtained from the blood and other body organs.

The anatomic features of the patient include appearance features such as body dimensions, face symmetry, hair and eye colour, skin texture, and the like. The physical features of the patient include walking speed, voice quality, speech attributes, speaking speed, and the like. The physiological features of the patient include sleep quality, digestion details, food preferences, weather preferences, and the like. The psychological features of the patient include anger and irritability, cognitive abilities, and the like. The blood pulse parameter may be a heart rate ranging from sixty to hundred beats per minute.

The health status computation subsystem 212 is configured to apply the collected patient information, the captured the phenotypic features, the one or more inputs and the blood pulse parameters associated with the patient on to a trained machine learning model and predict real time set of traditional medicine system parameters based on the results of the trained machine learning model. The health status computation subsystem 212 is further configured to dynamically map each of the patient information with the captured phenotypic features, the one or more inputs and the blood pulse parameters associated with the patient, validate each of the patient information, the captured the phenotypic features, the one or more inputs and the blood pulse parameters based on the trained machine learning model rules, generate a confidence score for each of the captured phenotypic features, the one or more inputs and the blood pulse parameters based on results of validation and predict the real time set of traditional medicine system parameters based on the generated confidence score.

The traditional medicine system parameters comprise prakriti level and vikriti level. The trained machine learning model helps in determining vikriti from the changes in Vata, Pitta and Kapha, dhatus (as defined in Ayurveda such as blood, muscle, fat, plasma, bone, bone marrow and the like) effected, and the like. The real time set of traditional medicine system parameters comprises Ayurveda variables or doshas, traditional Chinese medicine variables, Unani variables and the like. The confidence score indicates the confidence in the decision of output of the trained machine learning model where the confidence score may be a number between zero and one. The prakriti level may be determined based on physical traits, physiological functioning such as digestion, excretion, moods, nature, and the like. The vikriti level may be based on changes in the body of the patient with an hour of the day, a season of the year and a chronological stage of life.

The disease identification subsystem 214 is configured to compare the real time set of traditional medicine system parameters with pre-stored real time set of traditional medicine system parameters. The disease identification subsystem 214 is further configured to identify a disease based on the compared results and based on pre-stored disease database. The disease identification subsystem 214 is further configured to generate a recommendation message to the patient based on the identified disease. The recommendation message comprises of health and disease condition of a patient, health parameters, therapeutic interventions, clinical interventions, one or more medical remedies, and treatment plan. The disease identification subsystem 214 is further configured to perform one or more operations based on the generated recommendation message and the patient prior approval. The one or more operations comprises generating alerts for the patient representatives, generating alerts for medical representatives, generating new treatment plan and generating new diet plan. The disease identification subsystem 214 is further configured to output the generated recommendation message and the one or more operations on the user interface. The health status computation subsystem 212 and the disease identification subsystem 214 is further configured to estimate dosha imbalance and dhatus effected. The health status computation subsystem 212 and the disease identification subsystem 214 is further configured to estimate baseline cun, guan and chi and imbalance in cun, guan, and chi. The examples of the disease may be common cold, diabetes, endometriosis, cancer, dengue, gastro diseases, and the like. The health parameters are body mass index of the patient, blood pressure of the patient and the like. The therapeutic inventions may include herbal medicine, an activity to relax a patient's mind which may be meditation, Vedic chanting and the like. The clinical interventions include vaccines, injury prevention, environmental alterations, and the like. The types of dosha may be Pitta, Kapha, and Vata doshas. The examples of dhatus include plasma, blood, muscle, fat, bone marrow, reproductive fluid, and the like. The cun, guan, and chi may be three pulse regions of a radial artery in a wrist of the patient.

The digital kiosk 100 further comprises a printing subsystem 216 configured to print the recommendation message and responses from one or more doctors.

Figure 3:
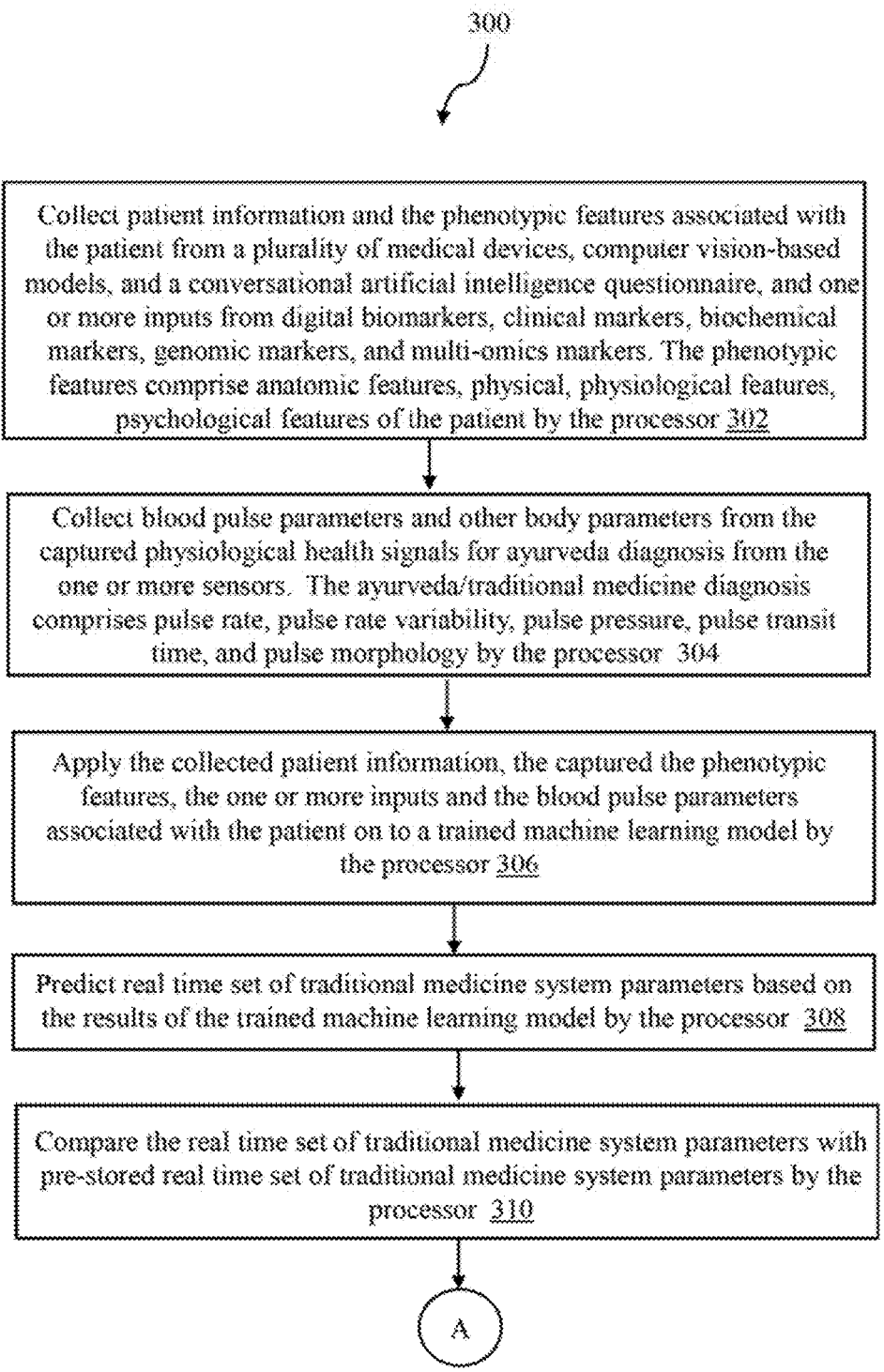
FIG. 3 is an exemplary process flowchart depicting a method for performing integrative analysis of health and disease condition of a patient using an AI based traditional data and modern data network, in accordance with an embodiment of the present disclosure.
Figure 3:
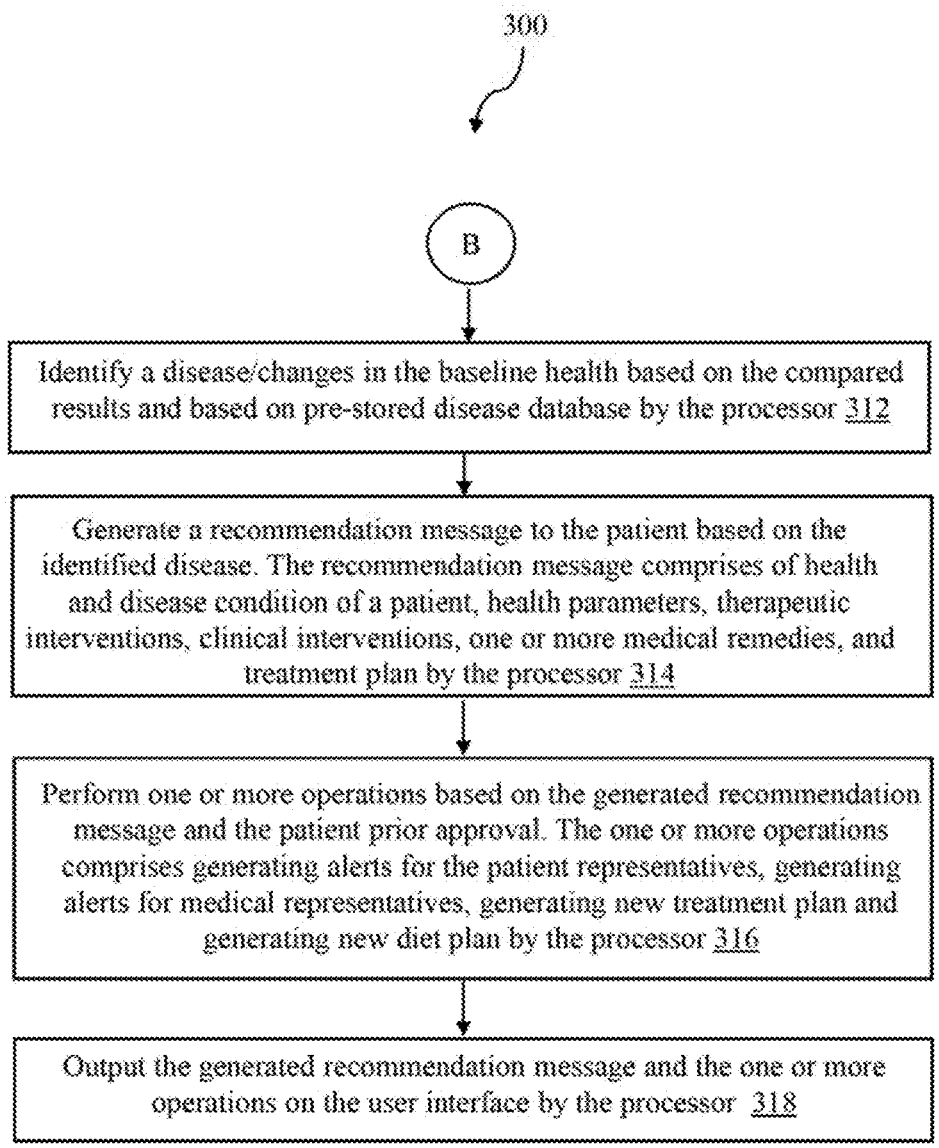

FIG. 3 is an exemplary process flowchart depicting a method 300 for performing integrative analysis of health and disease condition of a patient using an AI based traditional data and modern data network, in accordance with an embodiment of the present disclosure. The method 300 comprises capturing phenotypic features associated with a patient using one or more computer vision-based models by an image capturing system. The AI based traditional network is utilized for integrative analysis of health and disease condition of the patient. The method 300 further comprises capturing physiological health signals associated with the patient by one or more health sensors 102.

At step 302, information and the phenotypic features associated with the patient are collected from a plurality of medical devices, computer vision-based models, and a conversational artificial intelligence questionnaire, and one or more inputs from digital biomarkers, digital biomarkers and modern markers comprising clinical markers, biochemical markers, genomic markers, and multi-omics markers. The phenotypic features comprise anatomic features, physical, physiological features, psychological features of the patient.

At step 304, blood pulse parameters and other body parameters are collected from the captured physiological health signals for ayurveda or traditional medicine system diagnosis from the one or more health sensors 102. The ayurveda or the traditional medicine system diagnosis uses blood pulse parameters such as pulse rate, pulse rate variability, pulse pressure, pulse transit time, and pulse morphology.

At step 306, the collected patient information, the captured the phenotypic features, the one or more inputs and the blood pulse parameters associated with the patient are applied on to a trained machine learning model.

At step 308, real time set of traditional medicine system parameters are predicted based on the results of the trained machine learning model.

At step 310, the real time set of traditional medicine system parameters is compared with pre-stored real time set of traditional medicine system parameters.

At step 312, a disease or changes in baseline health is identified based on the compared results and based on pre-stored disease database.

At step 314, a recommendation message to the patient is generated to the patient based on the identified disease. The recommendation message comprises of health and disease condition of the patient, health parameters, therapeutic interventions, clinical interventions, one or more medical remedies, and treatment plan.

At step 316, one or more operations is performed based on the generated recommendation message and the patient prior approval. The one or more operations comprises generating alerts for the patient representatives, generating alerts for medical representatives, generating new treatment plan and generating new diet plan.

At step 318, the generated recommendation message and the one or more operations are outputted on the user interface.

The method 300 further comprises dynamically mapping each of the patient information with the captured phenotypic features, the one or more inputs and the blood pulse parameters associated with the patient, validating each of the patient information, the captured the phenotypic features, the one or more inputs and the blood pulse parameters based on the trained machine learning model rules, generating a confidence score for each of the captured phenotypic features, the one or more inputs and the blood pulse parameters based on results of validation and predicting the real time set of traditional medicine system parameters based on the generated confidence score.

The method 300 further comprises capturing one or more images of the patient, pre-processing the one or more images to extract the phenotypic features of the patient using the computer vision-based models and transmitting the extracted phenotypic features to the medical input data collection subsystem 210.

The method 300 further comprises displaying the conversational artificial intelligence questionnaire to the patient and receive one or more responses to the conversational artificial intelligence questionnaire from the patient. The conversational artificial intelligence questionnaire is generated at real-time based on the patient information and patient responses to the conversational artificial intelligence questionnaire.

Figure 4:
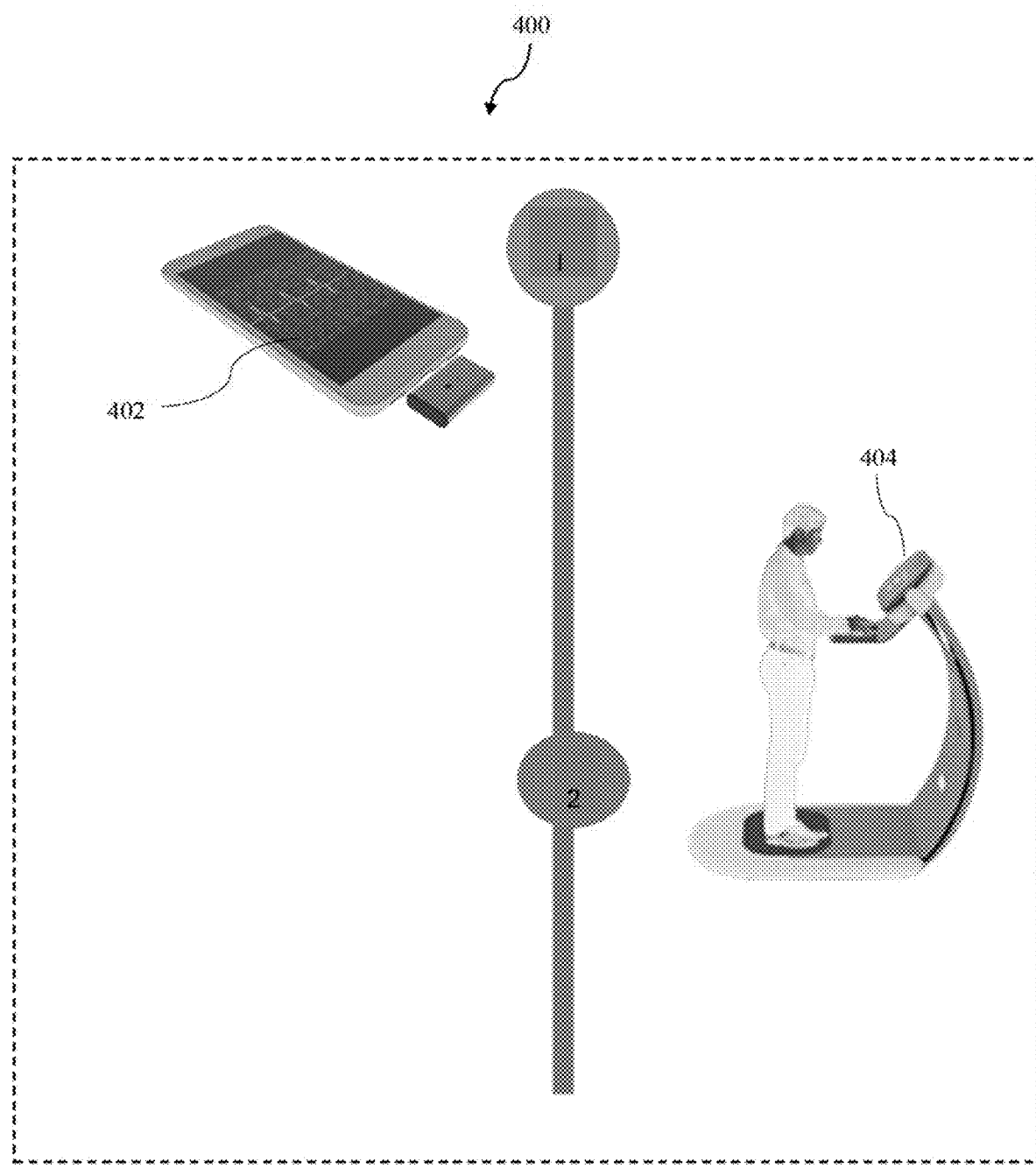
FIG. 4 is a schematic representation of a multi-device based deployable Ayurveda application, in accordance with an embodiment of the present disclosure.

FIG. 4 is a schematic representation 400 of a multi-device based deployable Ayurveda application, in accordance with an embodiment of the present disclosure. The web-based Ayurveda application is deployable on multiple devices such as a smart phone application 402 present on a device, and a digital kiosk 404. The digital kiosk 404 is utilized to perform for Ayurveda parameter assessment. The information may be transferred to the smart phone application 402 present on the device. FIG. 4 also schematically represents transfer of information between a smart phone application (1) and a digital kiosk (2).

Figure 5:
FIG. 5 is a tabular representation depicting a prakriti determination, in accordance with an embodiment of the present disclosure.

FIG. 5 is a tabular representation depicting a prakriti determination 500, in accordance with an embodiment of the present disclosure. A four-dimensional phenotypic assessment is performed using a conversational questionnaire which comprises anatomical, physical, physiological, and psychological features. An Artificial Intelligence (A) based framework is utilized for the prakriti determination 500. Firstly, four-dimensional phenotypic features are converted to categorical variables. A reference prakriti label is given by an Ayurveda doctor. Further, a random forest-based machine learning algorithm is trained to predict prakriti accurately. Further, hyper parameters such as number of trees, depth of the tress, loss function and the like are optimized to obtain a best accuracy of classification. An algorithm is trained on more than two hundred people cohort data. Based on the tabular representation, results depict a five-fold classification accuracy greater than ninety percentage for the prakriti determination 500 into the mixed prakriti classes of Vata-pitta (VP), Pitta-Kapha (PK) and Vata-Kapha (VK). The accuracy may be further improved by using more datasets and by using advanced deep learning and ensembled learning algorithms.

Figure 6:
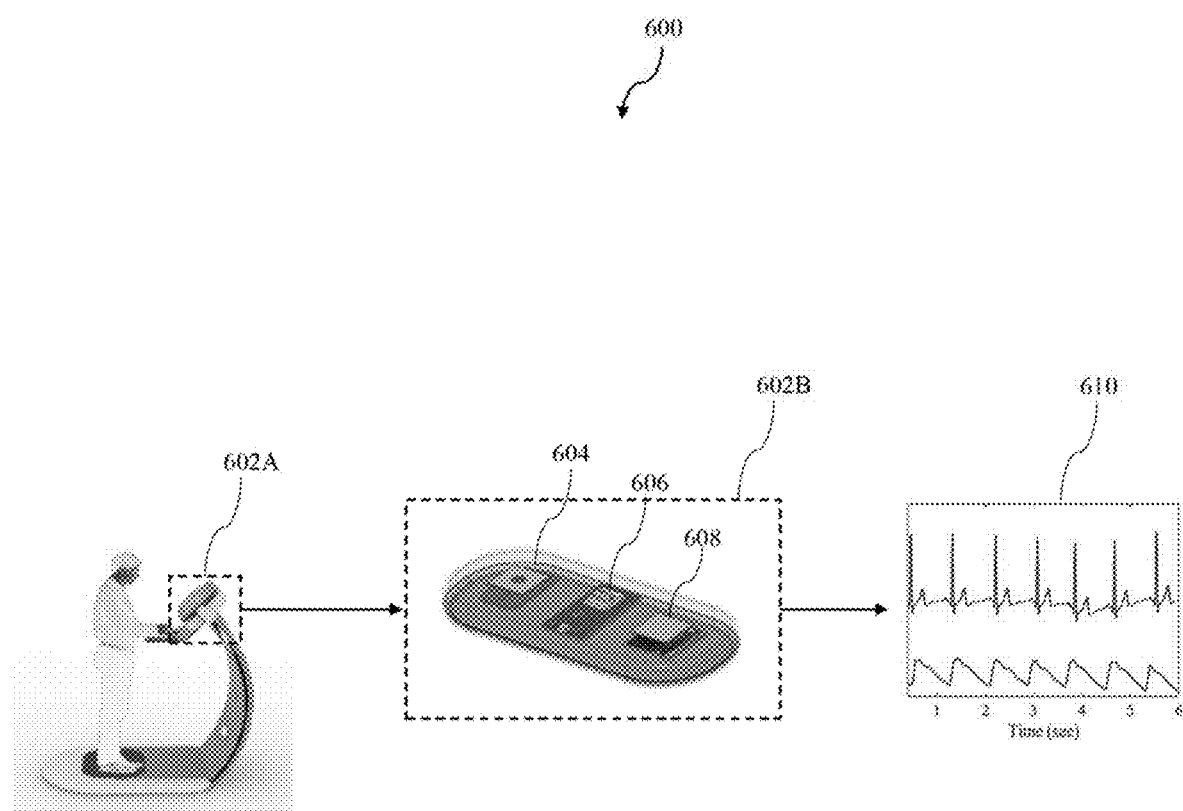
FIG. 6 is a schematic representation depicting a digital pulse diagnosis for a vikriti determination, in accordance with an embodiment of the present disclosure.

FIG. 6 is a schematic representation depicting a digital pulse diagnosis 600 for a vikriti determination, in accordance with an embodiment of the present disclosure. An ECG sensor 604 and a PPG sensor 608 are present on a digital kiosk 602 A-B. A microcontroller such as ESP32 606 is attached with the ECG sensors 604 and the PPG sensor 608. The top of the ECG sensor 604 has a metallic lead with a hole for collecting ECG signal and an optical sensor is present underneath the hole for collecting PPG signals. A pulse morphology, a heart rate and heart rate variability features are extracted for the vikriti determination. Further, obtained signals are pre-processed with suitable bandpass filters and other signal processing algorithms to provide noise corrected data 610. Additionally, signal quality index may also be assessed for rejecting noisy signals. The pulse morphology, the heart rate and the heart rate variability features are extracted from the captured signals (also referred as the noise corrected data 610).

Figure 7:
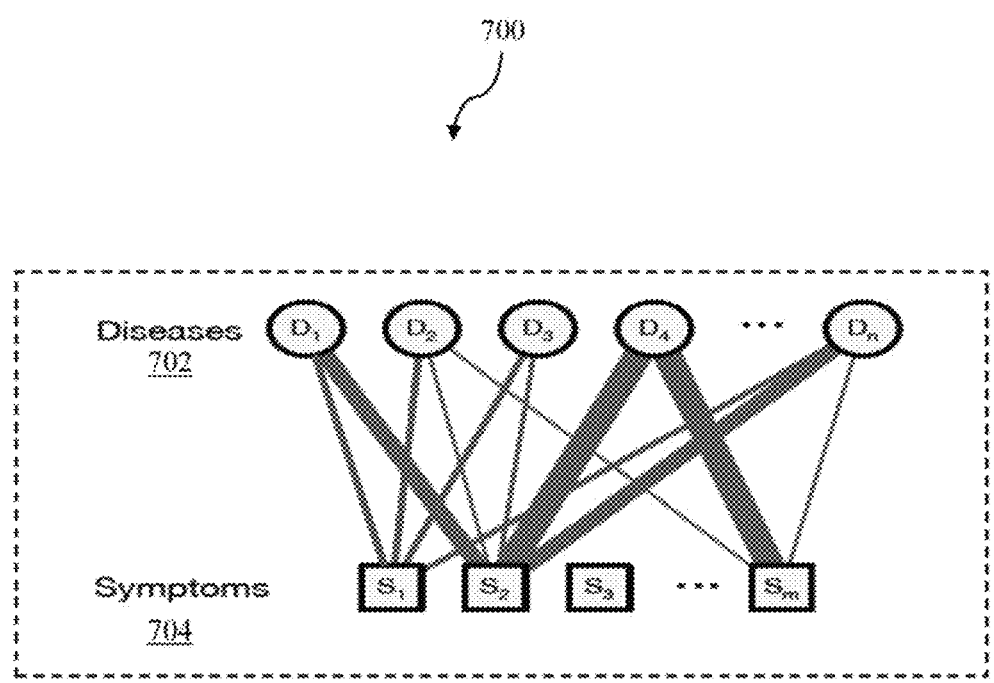
FIG. 7 is a graphical representation depicting an ayurveda symptom disease association network for performing integrative analysis of health and disease condition of a patient, in accordance with an embodiment of the present disclosure.

FIG. 7 is a graphical representation depicting an ayurveda symptom disease association network 700 for performing integrative analysis of health and disease condition of a patient, in accordance with an embodiment of the present disclosure. The ayurveda symptom disease association network is constructed from more than five hundred diseases 702 (also referred as diseases) as described in Ayurveda and more than six thousand symptoms 704 (also referred as symptoms).

Figure 8:
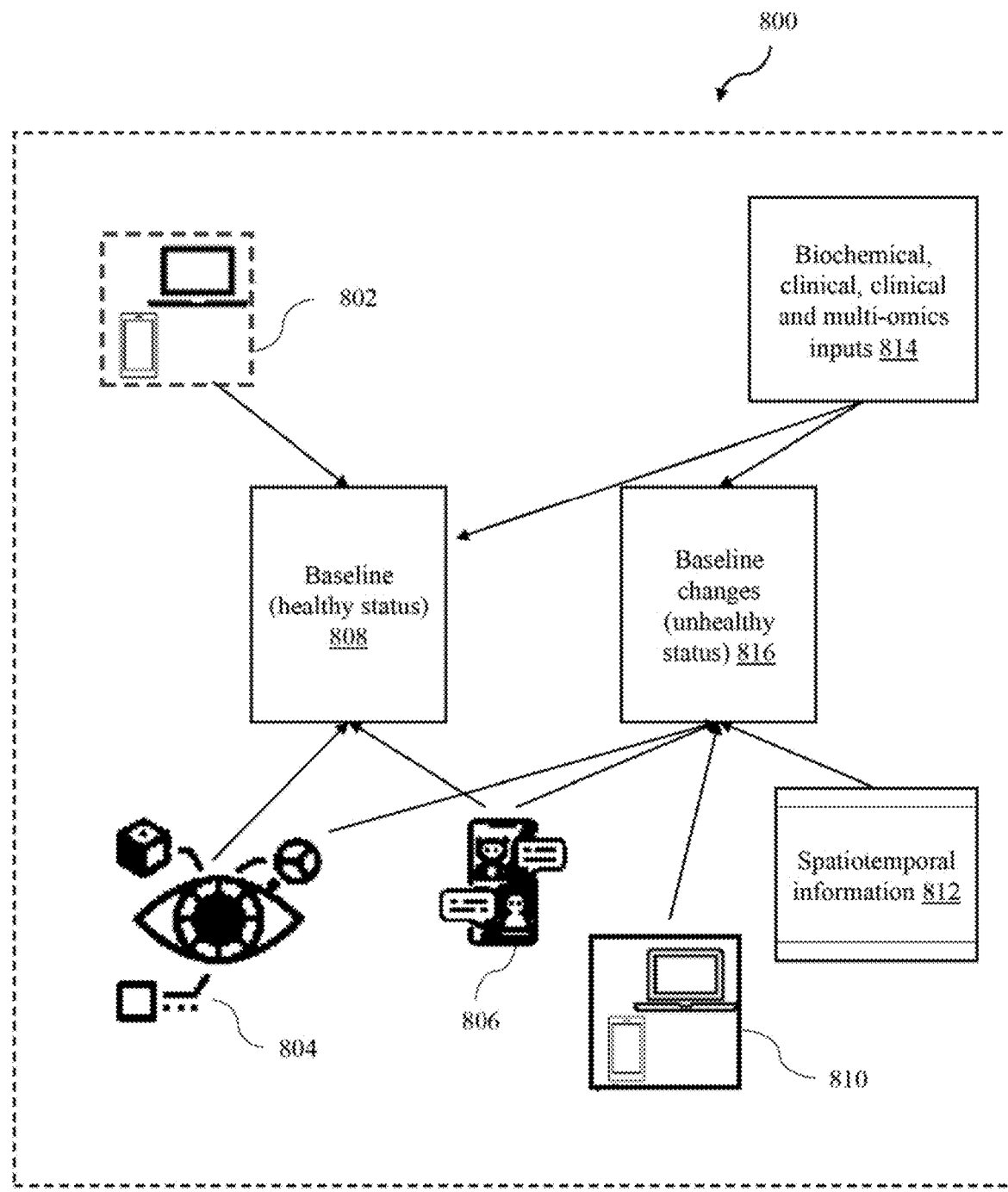
FIG. 8 is a block diagram of exemplary process depicting an integrative approach to determine baseline and baseline changes, in accordance with an embodiment of the present disclosure.

FIG. 8 is a block diagram of exemplary process depicting an integrative approach 800 to determine baseline 808 and baseline changes 816, in accordance with an embodiment of the present disclosure. The baseline 808 depicting a health state of a patient is generated using inputs 802 from digital devices, biochemical, clinical, multi-omics markers inputs 814 and computer vision techniques 804. In this case, the computer vision techniques 804 are used to capture anatomic, physiological features. The digital devices are used for determining the inputs 802 such as physiological parameters, sleep activities, eating patterns and the like of the patient. Further, certain biochemical, clinical, multi-omics markers inputs 814 are also used to establish the baseline 808 of the patient.

For a baseline estimation of the patient, a set of questionnaires 806 is also used in combination. The set of questionnaires 806 is used for capturing patient information and phenotypic features. The patient information includes age of the patient, gender of the patient, family history of the patient and the like. The phenotypic features include the anatomic features, physical features, physiological features, psychological features, and the like. The set of questionnaires 806 may be presented to the patient in a digital format using one or more external devices 106 such as computers, phones, tablets, smart watches, and the like. The one or more external devices 106 may be connected (wired or wirelessly) to a digital kiosk 100

The input from the set of questionnaires 806 is combined with the inputs 802 from the digital device and biochemical, clinical, and multi-omics markers inputs 814. The integrative approach 800 determines an accurate baseline (also referred as baseline 808) of patient health.

Further, the baseline changes 816 of the patient is established. Further, inputs 810 are captured from various digital medical devices, the computer vision techniques 804, biochemical, clinical, and multi-omics markers inputs 814. The digital medical devices capture the inputs 810 such as various physiological parameters comprising electrocardiogram (ECG), photo plethysmograph (PPG), electroencephalogram (EEG), sleep activity, physical and mental activities, eating patterns, environmental parameters, and the like of the patient. Additionally, the digital medical devices may also capture the inputs 810 such as multispectral reflectance, multispectral transmittance, multispectral autofluorescence using multispectral light sources and sensors (such as LEDs and photo detectors) from various body parts to understand various key parameters such as blood glucose and the like. Both static and dynamic digital biomarkers are captured to accurately establish the baseline changes 816.

The biochemical, clinical, and multi-omics inputs 814 includes data from blood tests, ultrasound, X-ray, CT, MRI, genome, exome, transcriptome, metabolome, epigenome, microbiome, proteome, glycome, and the like. A spatiotemporal information 812 is also collected in real time which includes information such as time of the day of symptoms, type of season, type of weather, geographical location of the patient, information on the gender and menstruation cycle, patient history and the like.

The input from the set of questionnaires 806 is combined with the inputs 810 from the digital medical devices, and the biochemical, clinical, and multi-omics inputs to determine the baseline changes 816. The spatiotemporal information 812 is also combined to understand the baseline changes 816. The baseline 808 and the baseline changes 816 are compared using an artificial intelligence-based comparison model to generate a health, wellness, disease risk-score. The artificial intelligence-based comparison model comprises machine learning and deep learning techniques. The health, wellness, disease risk-score indicates the health status of the patient in terms of traditional medicine variables such as Ayurveda variables which is Vata, Pitta and Kapha, Ayurveda diseases, traditional Chinese medicine variable such as Cun, Guan and Chi, traditional Chinese medicine diseases and (or) integrative system variables such as cardiovascular score, renal score, metabolic score, biological aging score and the like. The health, wellness, disease risk-score indicates diagnosis of a Roga (or) diseases of the patient and thus helps generate a suitable recommendation message to the patient. The health, wellness, disease risk score is a number ranging between, for example, 0 to 100, where 0 indicates least score and 100 indicates highest scoring and better health condition.

Figure 9:
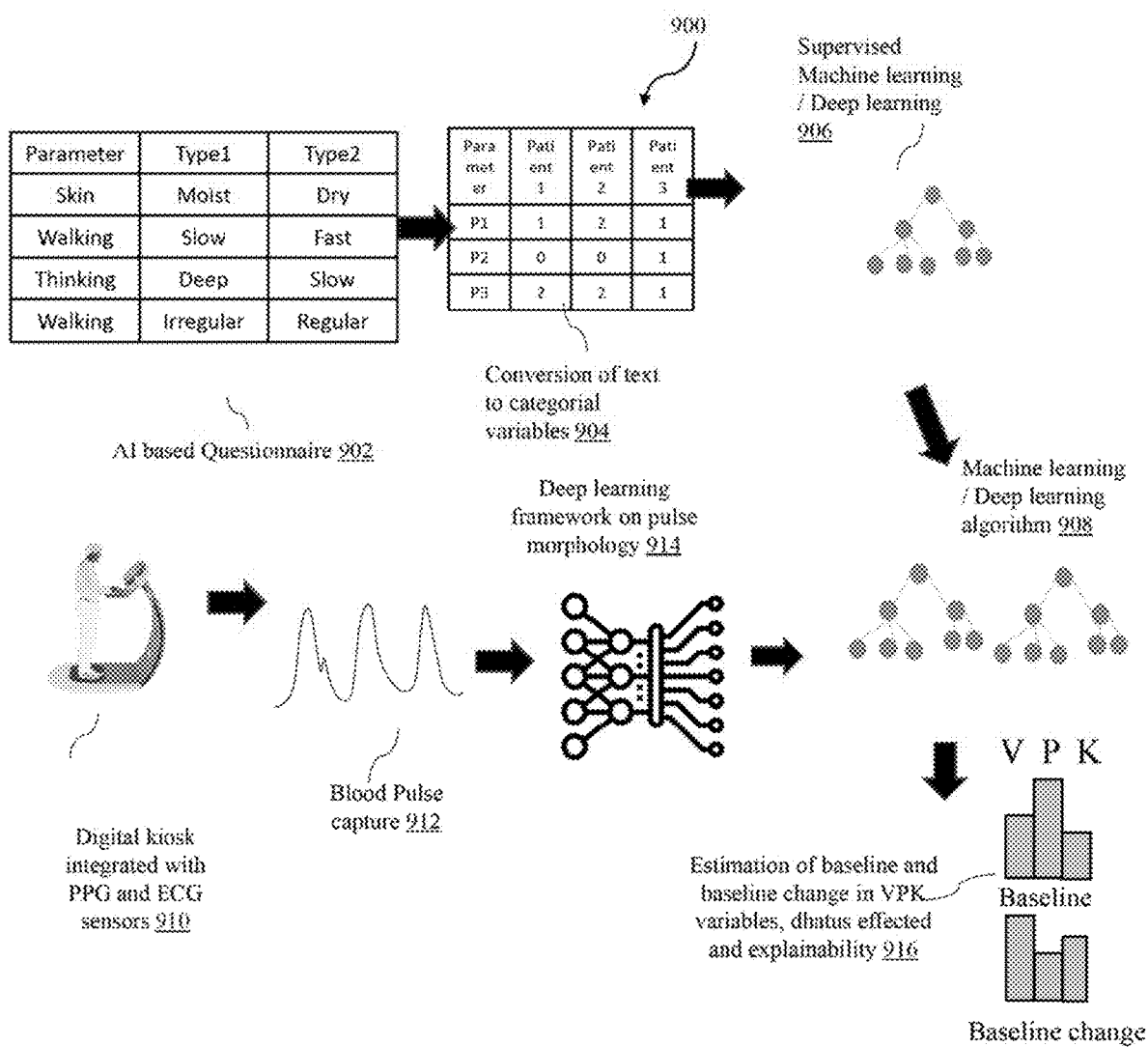
FIG. 9 is a schematic representation depicting a digital kiosk-based approach for prakriti and vikriti determination, in accordance with an embodiment of the present disclosure.

FIG. 9 is a schematic representation depicting a digital kiosk-based approach 900 for prakriti and vikriti determination, in accordance with an embodiment of the present disclosure. As used herein, the term "feature" refers to different phenotypic parameters of a patient, such as physical, psychological, anatomical, physiological, for example, skin colour, digestion, thinking, walking and the like. In another embodiment, firstly a set of adaptive and conversational artificial intelligence-based questionnaire 902 is collected. The set of adaptive and conversational artificial intelligence-based questionnaire 902 includes questions related to the features of an individual such as characteristics of eyes, ears, hair, hands, and the like. The set of adaptive and conversational artificial intelligence-based questionnaire 902 further comprises questions related to disease symptoms such as pain in certain part of a body, sleep disorders, changed body weight, excessive thirst or urination and the like. The set of adaptive and conversational artificial intelligence-based questionnaire 902 may also include questions related to causative factors for the symptoms such as eating certain foods, exposure to environmental factors dust, infections and the like physical and mental stress, consumption of certain medication and the like. These set of adaptive and conversational artificial intelligence-based questionnaire 902 are in text format. The text of the set of adaptive and conversational artificial intelligence-based questionnaire 902 is converted to categorical variables 904 such as 0s and 1s in a matric form. Furthermore, a supervised machine learning algorithm 906 is applied onto each of these categorical variables 904 to estimate 916 baseline Vata, Pitta and Kapha and explain ability is given for easy interpretation of the results.

Simultaneously, a digital device such as a digital kiosk 910 is included. The digital kiosk 910 is integrated with a photo plethysmograph (PPG) sensor 118, an electrocardiogram (ECG) sensor 114 and a galvanic skin response (GSR) sensor. Alternatively, the camera of the digital kiosk 910 may be used to collect the video plethysmograph data. This digital kiosk 910 captures the physiological parameters such as blood pulse 912 of a patient. Additionally, inputs from one or more health sensors 102 in the digital device such as accelerometer, gyro meter and the like are used to compensate for various noises. The physiological parameters are applied to a trained deep learning framework 914. The model also considers various confounding factors such as time of the day, season, weather, sleep habits, stress levels and the like are captured using the digital device. The outputs from the trained deep learning framework 914 are further given to a machine learning or deep learning algorithm 908 for baseline 808 and baseline changes 816 in Vata, Pitta and Kapha variables, dhatus effected and explainability in terms of features contributing to the baseline 808 and the baseline changes 816 are given for easy interpretation of the results. In an exemplary embodiment, the integrative system provides a web-based Ayurveda application deployable either independently or together onto multiple devices such as a smart phone, smart computer, smart tablet, a smart band, and the digital kiosk 910 and the like.

Figure 10:
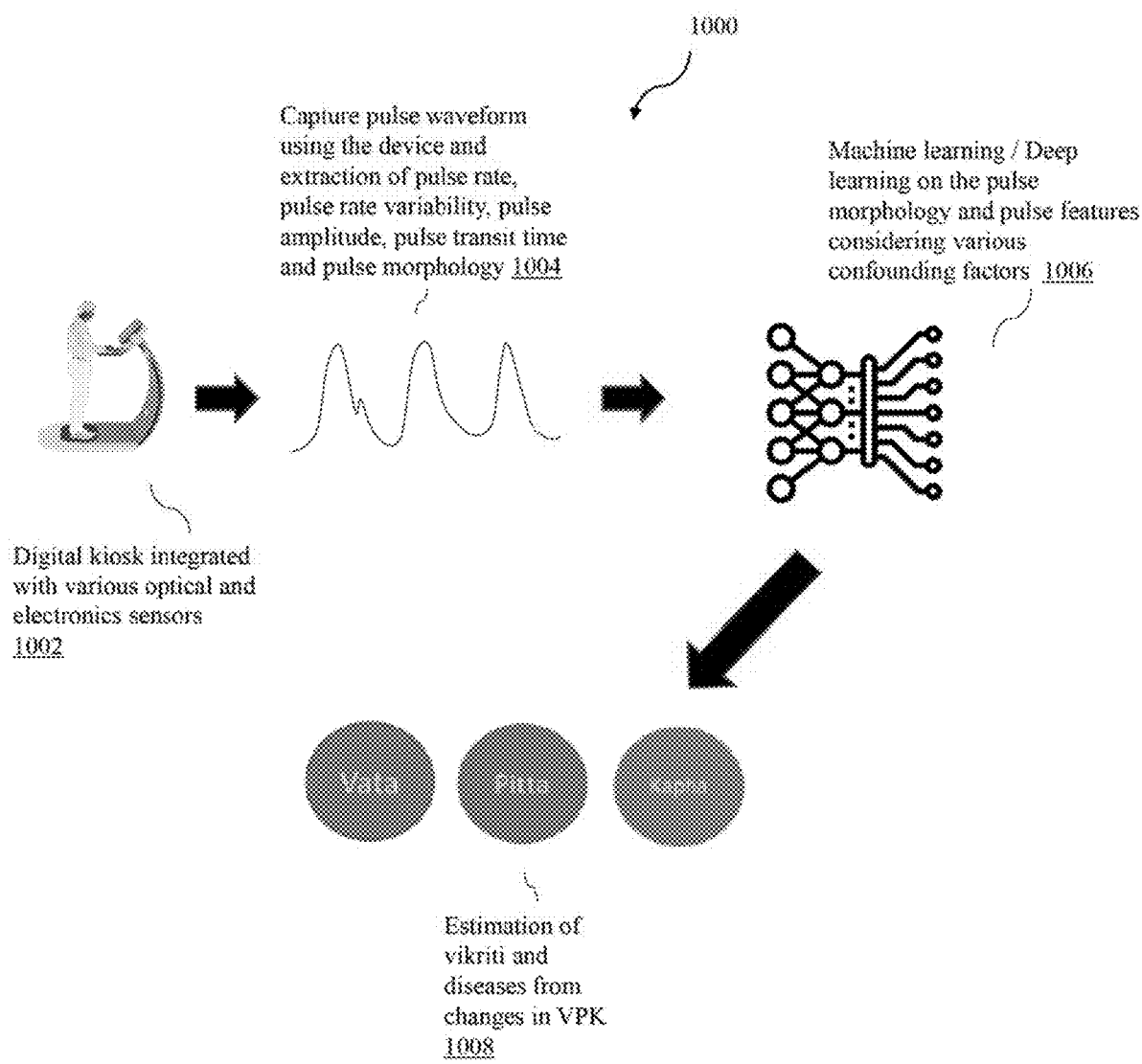
FIG. 10 is a schematic representation depicting pulse diagnosis for Ayurveda Vikriti, in accordance with an embodiment of the present disclosure.

FIG. 10 is a schematic representation 100 X) depicting pulse diagnosis for Ayurveda Vikriti, in accordance with an embodiment of the present disclosure.

A digital device, such as a digital kiosk 1002 is integrated with various optics and electronics sensors such as a photoplethysmography sensor 118, an electrocardiogram sensor 114, an accelerometer, a barometer, a bioimpedance, a galvanic skin response, gyrometer and the like which comprises various noises. This digital kiosk 1002 captures a pulse waveform 1004 of a person and the inputs from one or more health sensors 102 is utilized to generate new digital biomarkers or compensate for influencing factors on the pulse waveform 1004. Features such as pulse rate variability, amplitude, transit time and pulse morphology are extracted from the pulse waveform 1004. Various machine learning and deep learning techniques 1006 are applied on extracted pulse features and the pulse morphology and considers various confounding factors such as time of the day, season, weather, sleep habits, stress levels and the like are captured using the digital device. The output of the machine learning and the deep learning techniques 1006 generates estimation 1008 of Vikriti based on changes in Vata, Pitta and Kapa.

Figure 11:
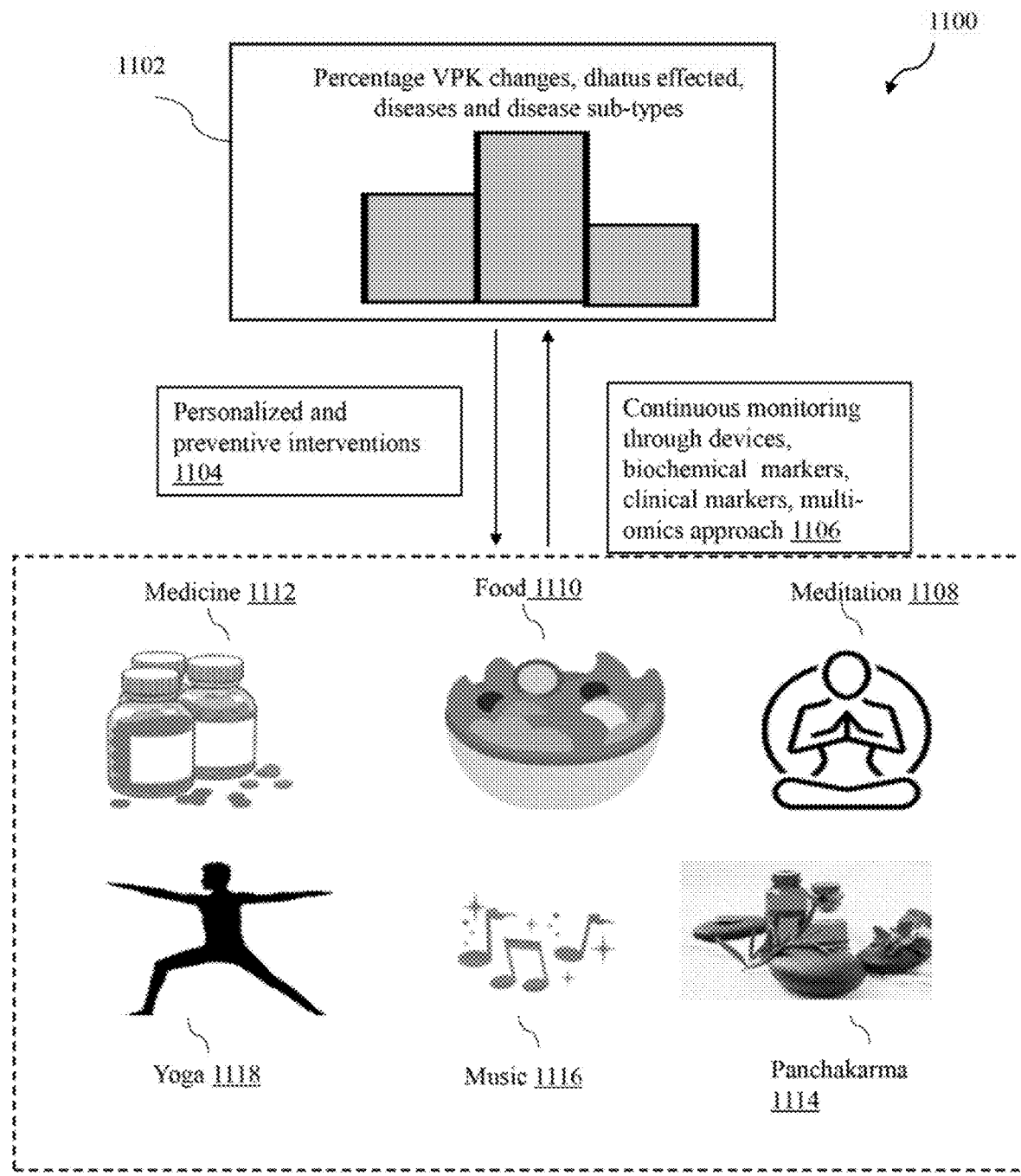
FIG. 11 is a schematic representation of depicting a process of determining therapeutic interventions from Ayurveda doshas in accordance with an embodiment of the present disclosure.

FIG. 11 is a schematic representation of depicting a process 1100 of determining therapeutic interventions from Ayurveda doshas 1102 in accordance with an embodiment of the present disclosure. From the Ayurveda doshas 1102 such as changes in Vata, Pitta, and Kapha (VPK), dhatus effected, Ayurveda diseases including disease sub-types, a personalized and preventive interventions 1104 and the like are determined. The therapeutic interventions include food 1110, medicine 1112, meditation 1108, yoga 1118, music 1116, panchakarma 1114 and the like such as Vedic chanting. In such an embodiment, a whole process 1106 of the therapeutic intervention is continuously monitored through devices, biochemical markers, clinical markers, and multi-omics approach. In such an embodiment, a supervised or un-supervised machine learning and deep learning techniques are applied to collect patient information and to extract digital biomarkers. The therapeutic interventions are tailored according to such monitored output.

Figure 12A:
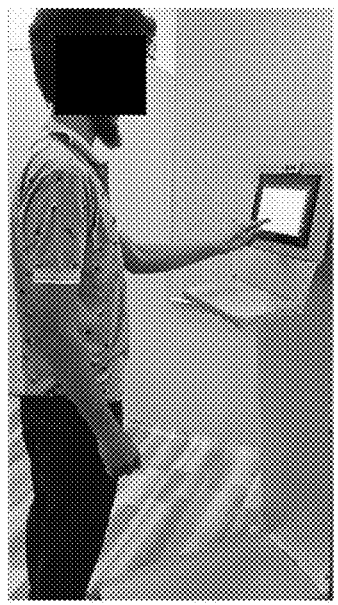
FIGS. 12A-C are pictorial representations depicting a prototype version of a digital kiosk, in accordance with an embodiment of the present disclosure.
Figure 12B:
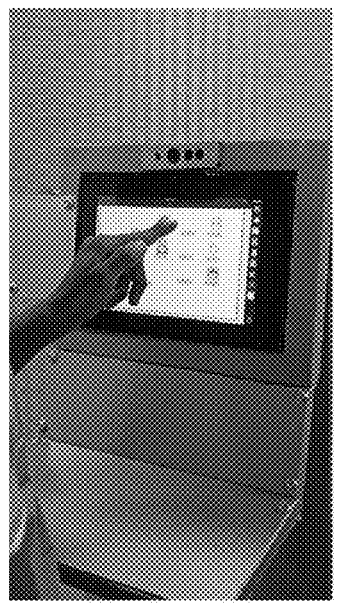
Figure 12C:
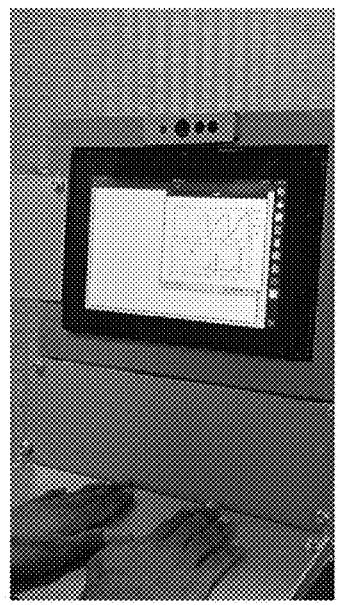

FIGS. 12A-C are pictorial representations 1200 A-C depicting a prototype version of a digital kiosk 100, in accordance with an embodiment of the present disclosure. Detailed explanation of the digital kiosk 100 is depicted in FIG. 1.

Figure 13:
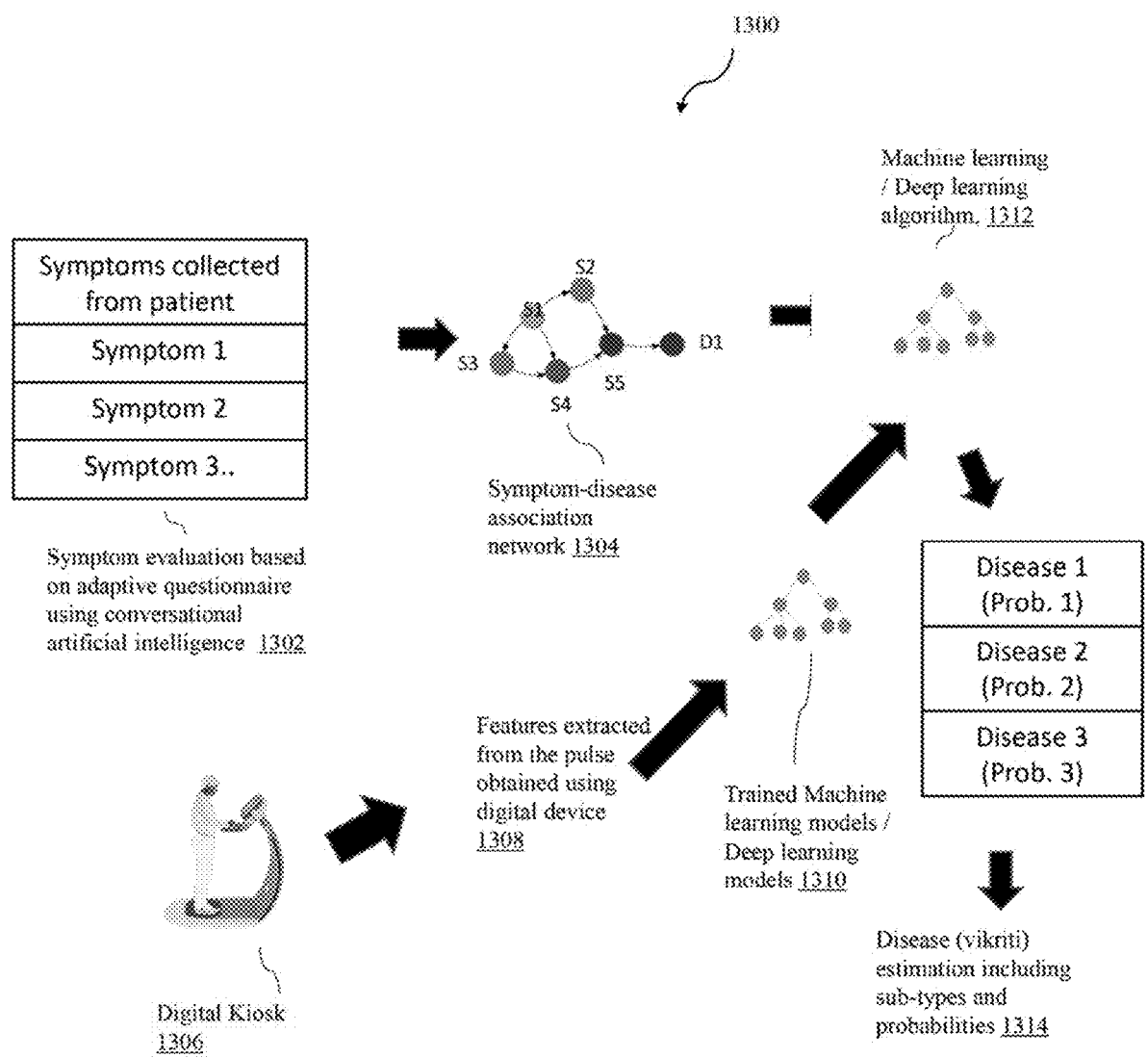
FIG. 13 is a schematic representation depicting an exemplary process of estimating Ayurveda vikriti, in accordance with an embodiment of the present disclosure.

FIG. 13 is a schematic representation depicting an exemplary process of estimating Ayurveda vikriti 1300, in accordance with an embodiment of the present disclosure. In such an embodiment, adaptive questionnaires 1302 based on conversational artificial intelligence comprises questions related to disease symptoms such as pain in certain part of a body, sleep disorders, changed body weight, excessive thirst or urination, and the like. The adaptive questionnaire 1302 is adaptive in such a way where a next question to understand a presence or absence of a particular symptom is presented based on response to a previous symptom. In a particular embodiment, the adaptive questionnaire 1302 is designed based on a symptom-disease association network 1304. These adaptive questionnaires 1302 are outputted to a patient on a patient's device for obtaining a response for each of these adaptive questionnaires 1302. The adaptive questionnaire 1302 helps in triaging the possible diseases of the patient based on the symptoms.

The responses of the adaptive questionnaire 1302 are compared with the symptom-disease association network 1304. The symptom-disease association network 1304 may be trained on various machine learning and deep learning models which is used to provide disease probability corresponding to certain symptoms. In one exemplary embodiment, a graph neural network may be used for outputting diseases along with probabilities corresponding to particular symptoms. In another embodiment, machine algorithms such as Bayesian networks are used for outputting diseases along with probabilities corresponding to particular symptoms.

Simultaneously, inputs from a digital kiosk 1306 are collected. In such an embodiment, the digital kiosk 1306 may have inbuilt sensors such as weight sensor, impedance sensor to measure the body fat and other compositions, camera to capture visual features and the like or attached with one or more health sensors 102 such as an ECG sensor 114, a PPG sensor 118, and the like. The digital kiosk 1306 is used to extract features 1308 such as pulse rate, pulse rate variability, nonlinear measures of the pulse rate variability, pulse pressure, pulse morphology, and the like. The features 1308 are also fed as an additional input to trained machine learning models 1310 to estimate the possible diseases along with explainable artificial intelligence framework in terms of the symptoms contributing to identification of a particular disease along with the probabilities of the diseases.

The outputs from the symptom-disease association network 1304 and the trained machined learning models 1310 are given as inputs to another machine learning algorithm or deep learning algorithm 1312. The machine learning algorithm or the deep learning algorithm 1312 aggregates the inputs and gives a decision on the Ayurveda diseases including disease sub-types with probabilities 1314.

Figure 14A:
Figure 14A:
Figure 14B:
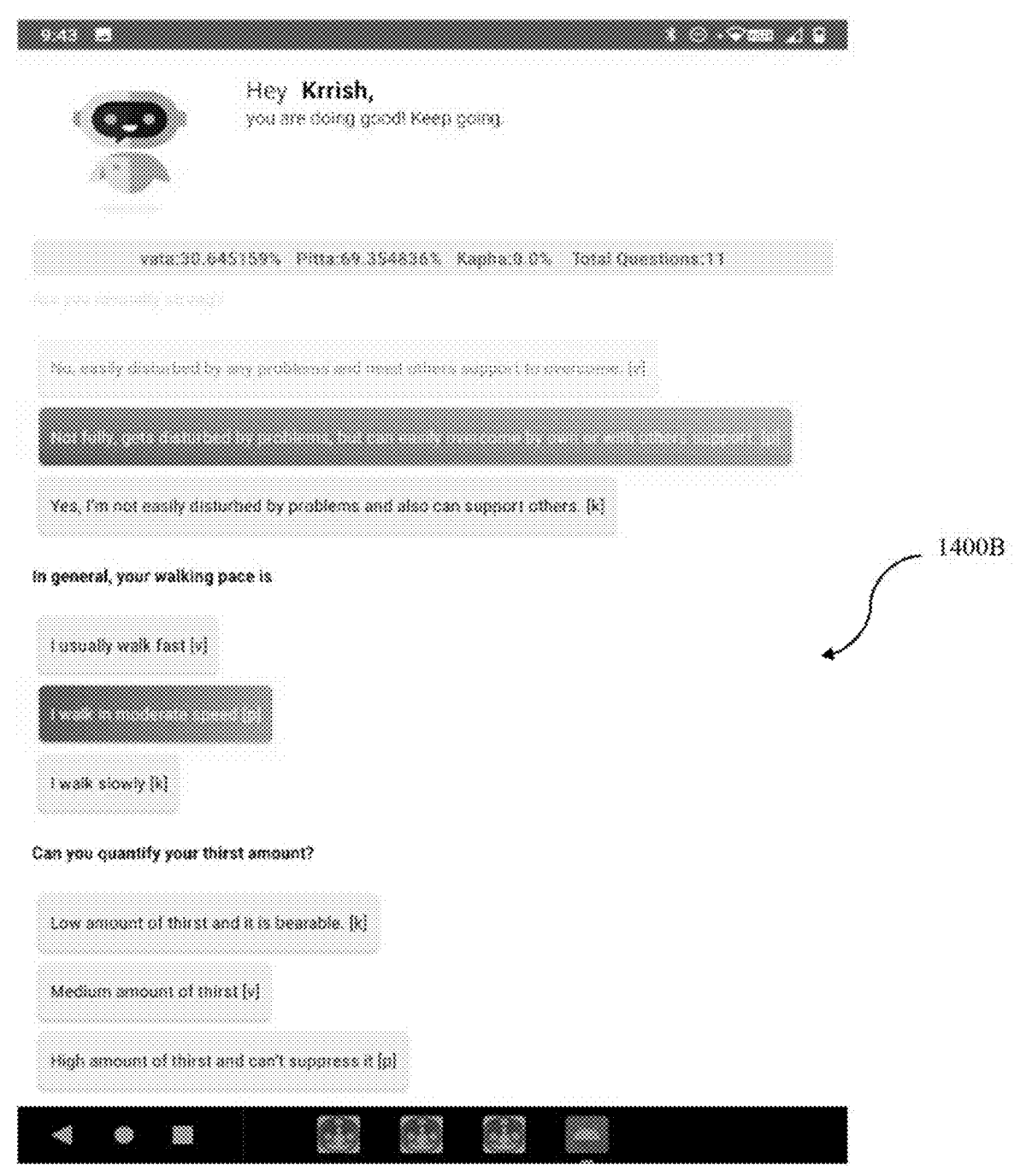
Figure 14C:

FIGS. 14A-C are graphical user interface of conversational artificial intelligence based adaptive questionnaire framework designed as per Ayurveda principles for assessing Prakriti baseline of a person 1400 A-C, in accordance with an embodiment of the present disclosure. Each question in a questionnaire probes Vata, Pitta or Kapha characteristics of the person based on phenotypic features. In this case, weights for each of the questions in the questionnaire are pre-assigned based on the clinical knowledge or from a machine learning algorithm. At the end of each questionnaire set of questionnaires, scores are calculated for the Vata, the Pitta and the Kapha.

FIGS. 14 B-C depicts the calculated scores of Vata, Pitta and Kapha. The questions are presented to the subjected till the successive difference in the scores from a conversational artificial intelligence based adaptive questionnaire or set of questionnaires is less than a pre-set threshold value. The conversational artificial intelligence based adaptive questionnaire saves significant time in assessing the prakriti (baseline) of any person while achieving the desired accuracy. Some of questions in the conversational artificial intelligence based adaptive questionnaire pertaining to prakriti estimation are "how you feel about your hair density?", "What's your normal speed of doing work?", "eye colour?", and the like. Similar conversational artificial intelligence-based framework may also be used for assessing the Vikriti (diseased state) of a person.

Figure 15A:
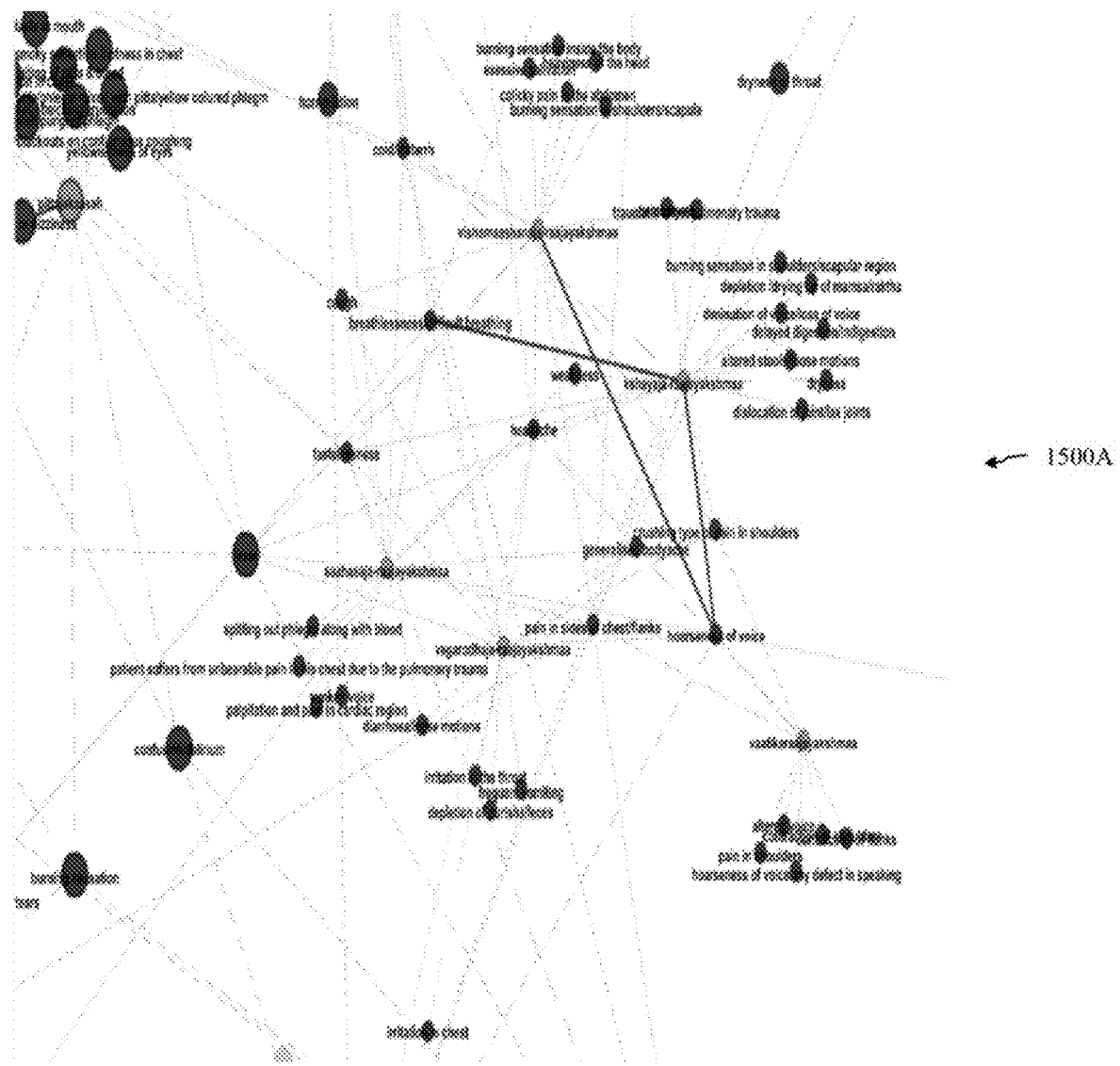
FIGS. 15A-B are snapshot representations of weights of associations between each symptom to the disease as trained using artificial intelligence techniques such as machine learning, probabilistic reasoning, graph neural networks in accordance with an embodiment of the present disclosure.
Figure 15B:
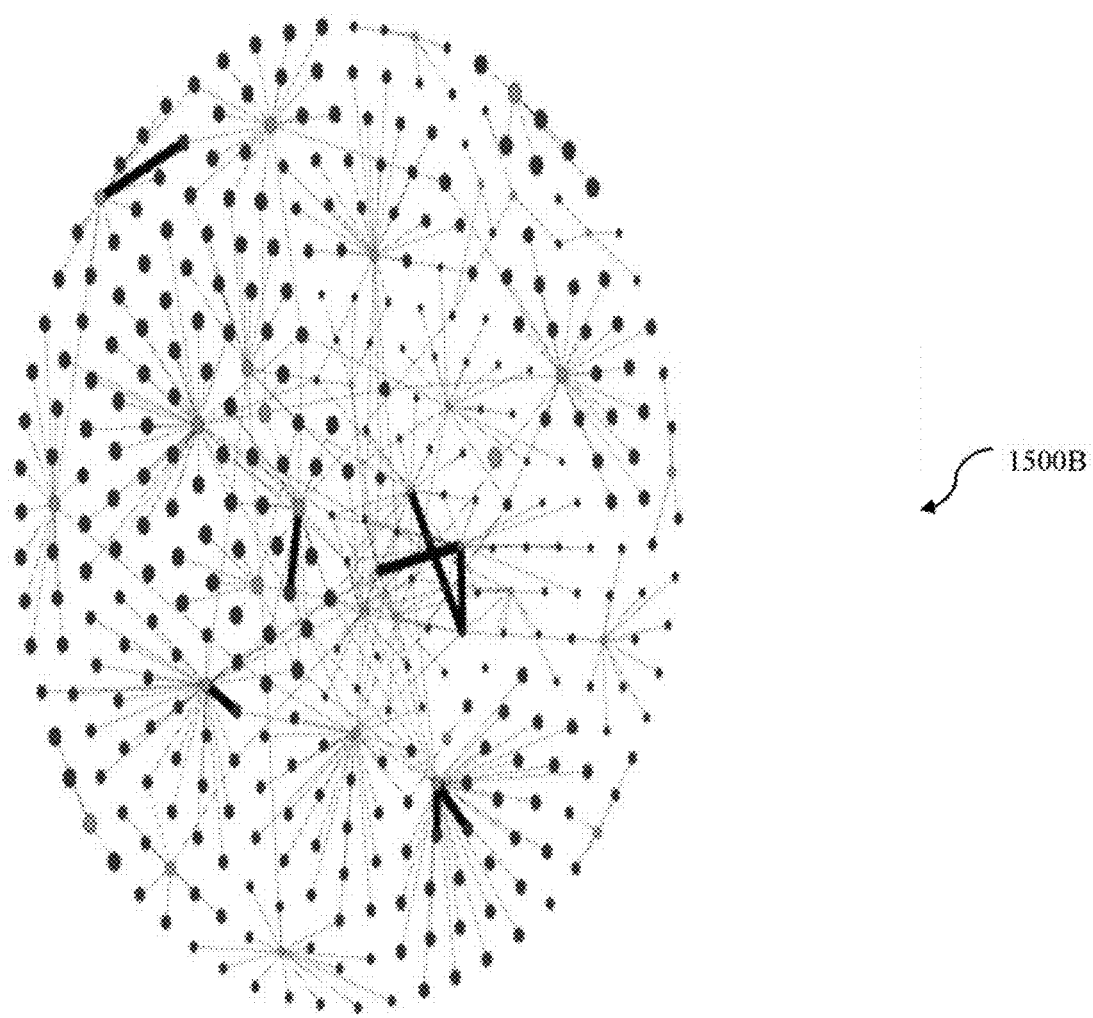
Figure 16A:
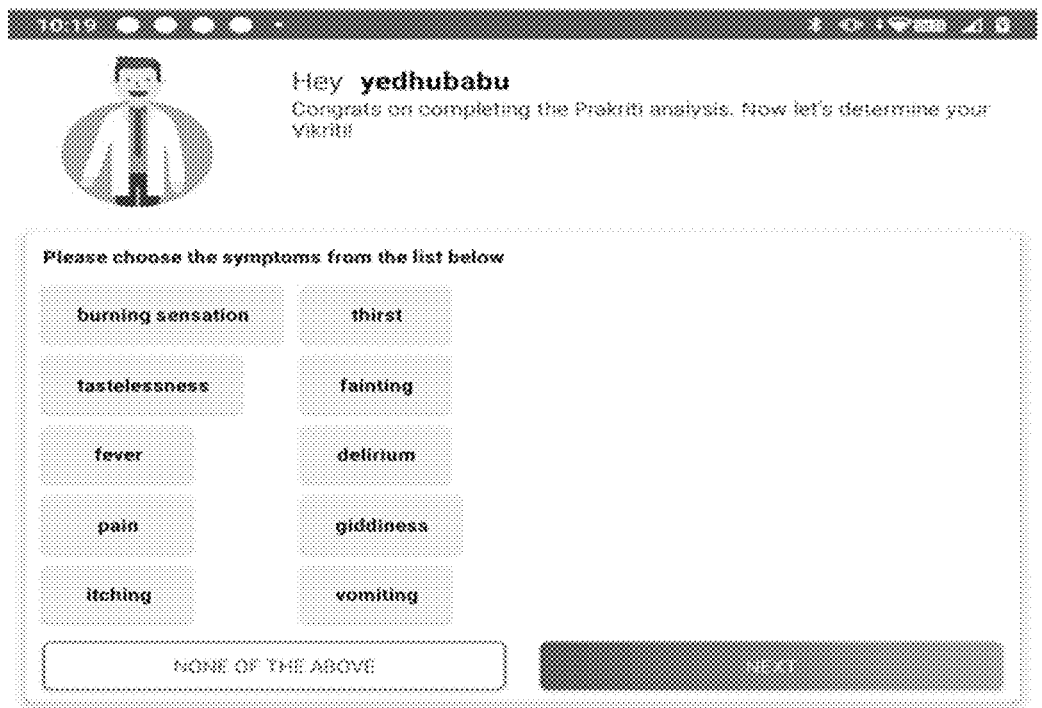
FIGS. 16A-D are graphical user interface of conversational artificial intelligence-based adaptive questionnaire framework designed as per Ayurveda principles for assessing vikriti (disease) of a person, in accordance with an embodiment of the present disclosure.
Figure 16B:
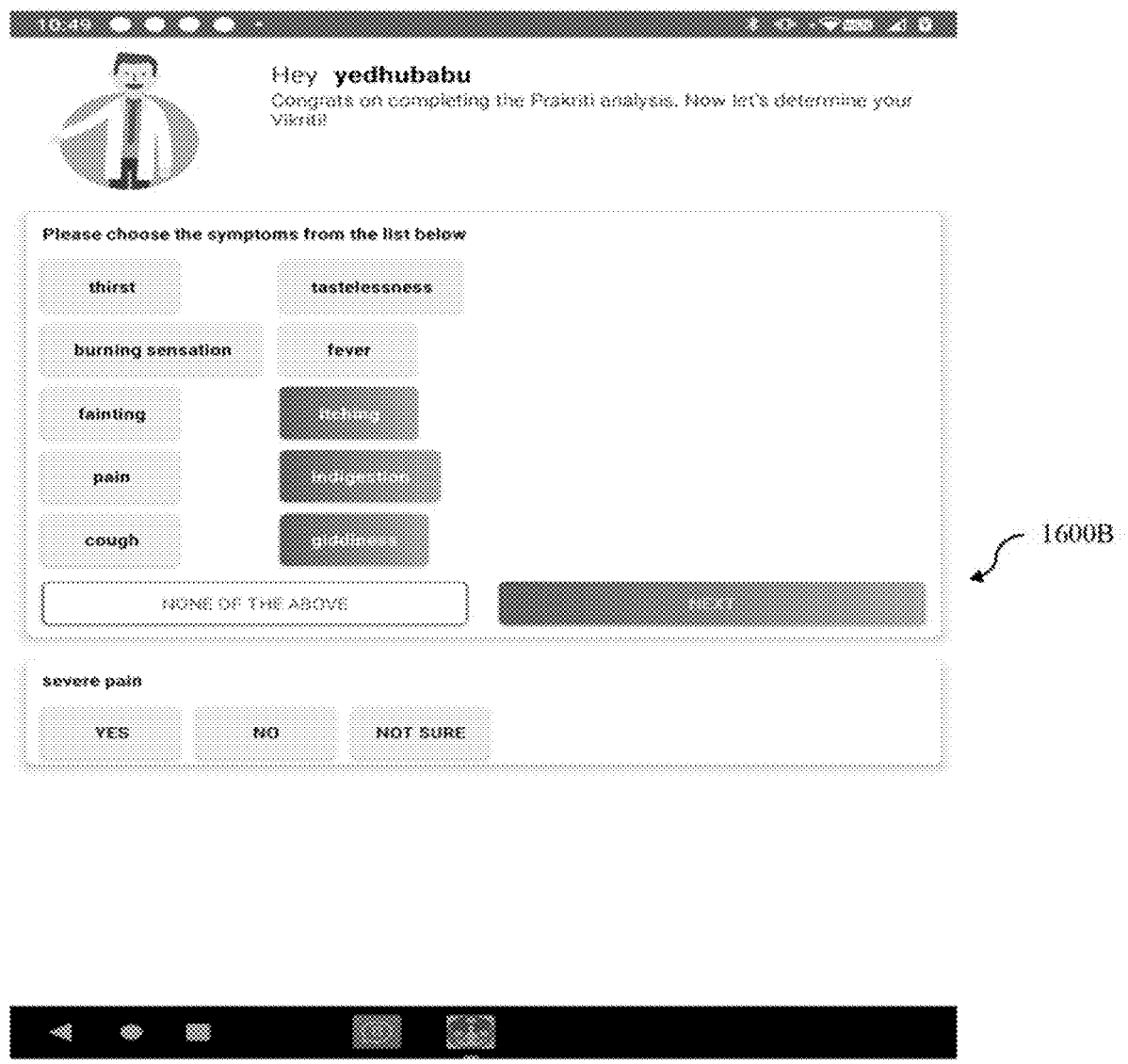
Figure 16C:
Figure 16D:
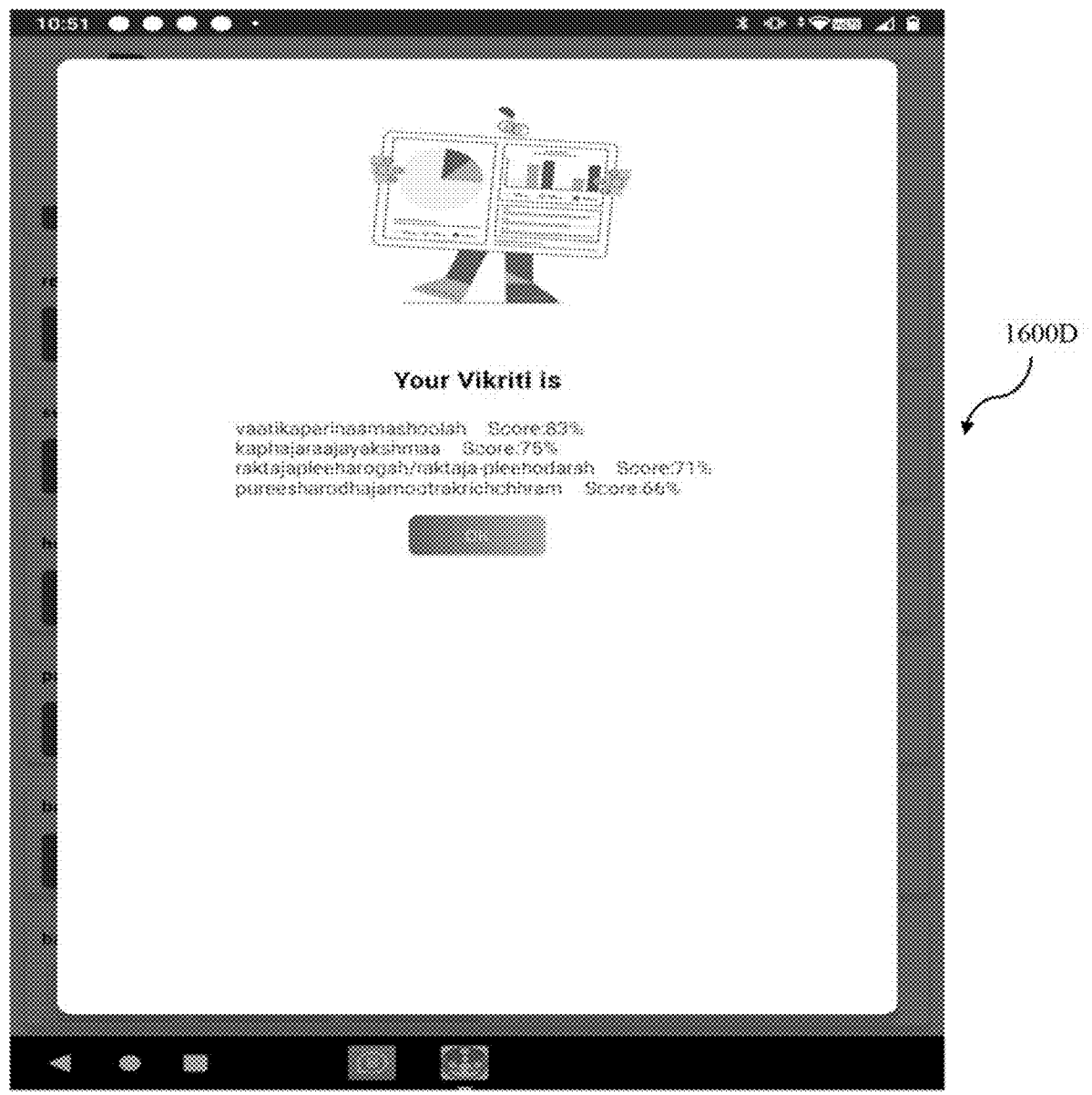

FIGS. 15A-B are snapshot representations 1500 A-B of weights of associations between each symptom to the disease as trained using artificial intelligence techniques such as machine learning, probabilistic reasoning, graph neural networks in accordance with an embodiment of the present disclosure. First a symptom-disease association network 1304 is built based on Ayurveda principles that relates symptoms to diseases. The weights of associations between each symptom to the disease are trained using artificial intelligence techniques using techniques such as machine learning, probabilistic reasoning, graph neural networks and the like. Snapshots of the symptom-disease association network 1304 demonstrates a relation between the symptoms and the diseases.

FIGS. 16A-D are graphical user interface 1600 A-D of conversational artificial intelligence-based adaptive questionnaire framework designed as per Ayurveda principles for assessing vikriti (disease) of a person, in accordance with an embodiment of the present disclosure. Subsequently, a patient is presented with various symptoms in an adaptive questionnaire form and depending on responses of the patient, a network triages a most probable set of diseases. Additionally, disease sub-types as described in Ayurveda are also predicted.

FIGS. 17A-I are various screenshot representations 1700 A-I depicting an exemplary process of a disease and health condition prediction, in accordance with an embodiment of the present disclosure. In this case, for example, the disease predicted may be such as but not limited to diabetes.

Figure 17A:
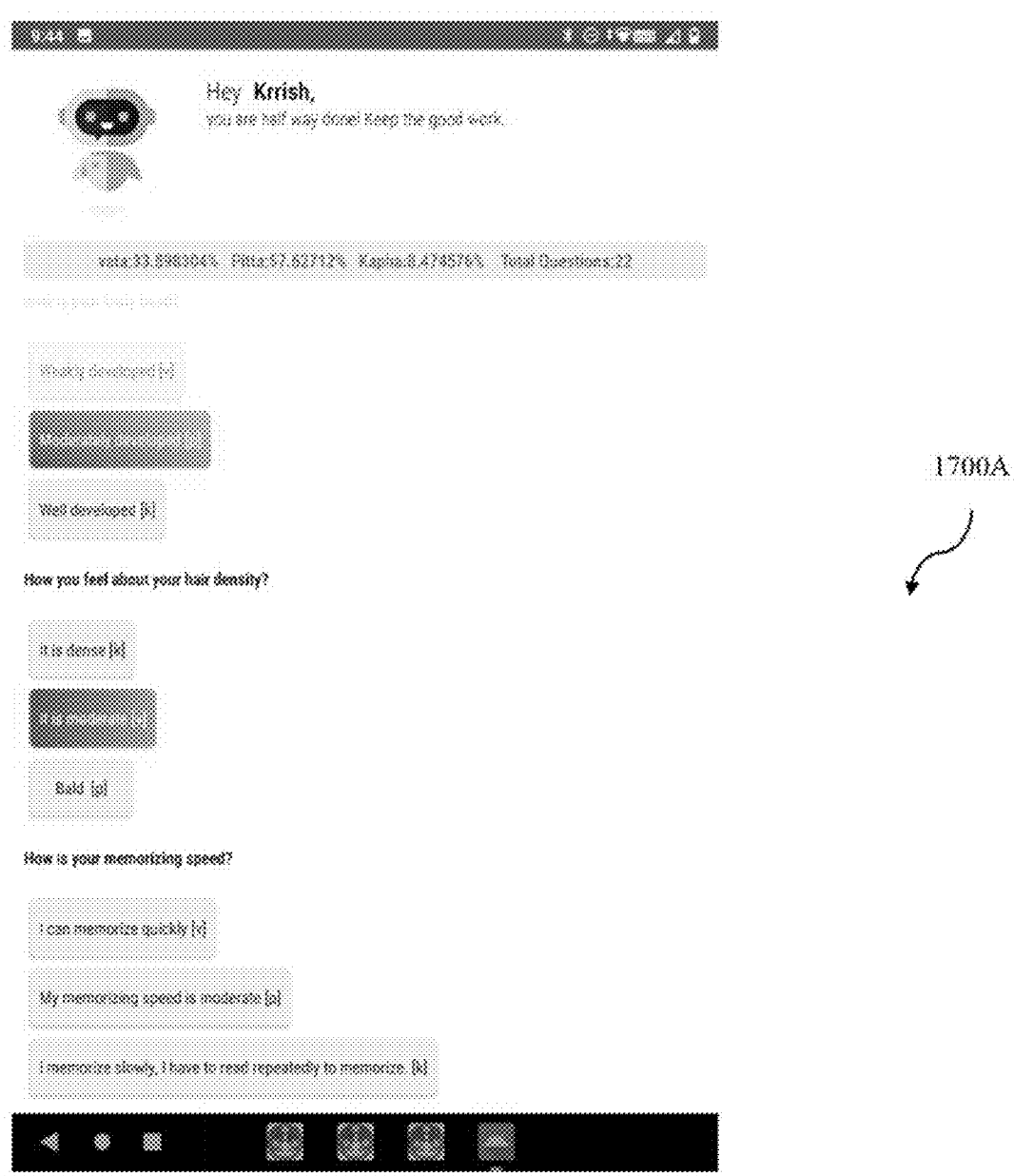
Figure 17C:
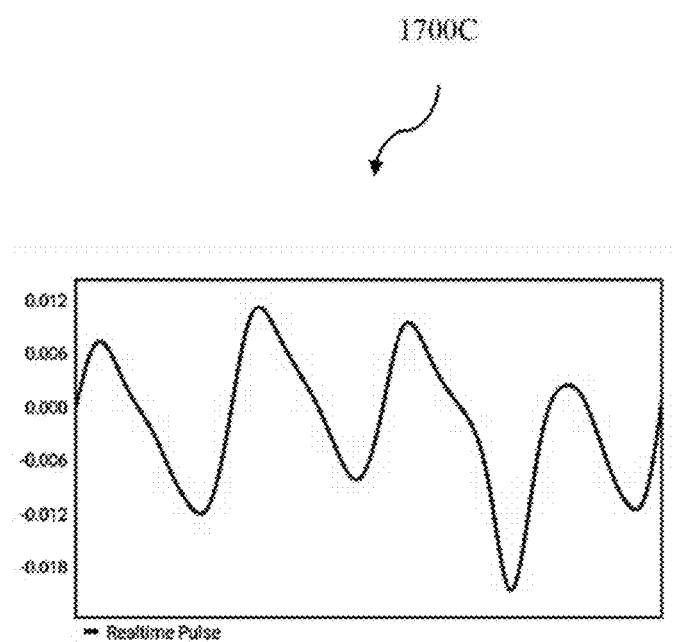
Figure 17D:
Figure 17E:
Figure 17F:
Figure 17G:
Figure 17H:
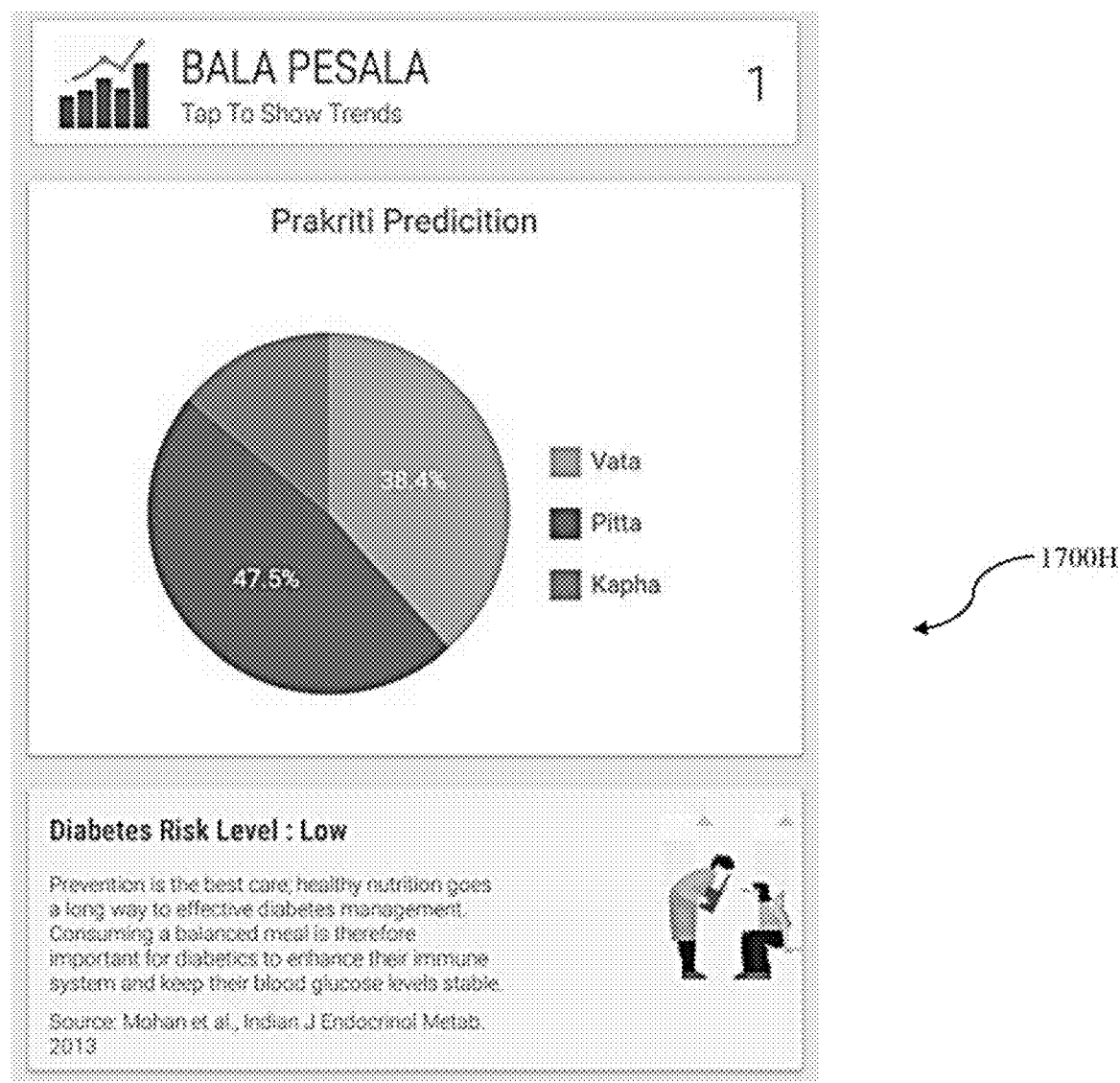
Figure 17I:

FIGS. 17A-B are pictorial representations depicting a process of collecting inputs using a conversational AI based questionnaire 1700 A-B, in accordance with an embodiment of the present disclosure. The one or more questions present in the conversational AI based questionnaire 1700 A-B comprises the one or more questions related to hair density of the person, memorizing speed of the person, body build of the person and types of symptoms of the disease of the person such as if the person has encountered any shortness of breath, stomach bloating, numbness of hands, urine discoloration, body pain and the like.

FIG. 17 C is a graphical representation 1700 C depicting a pulse of the person, in accordance with an embodiment of the present disclosure. The pulse of the person is collected using digital sensors. The collected patient data, symptoms and parameters extracted from the digital sensors comprises heart rate and heart rate variability of more than hundred individuals. Further, the collected patient data, the symptoms and the parameters may be trained using random forest algorithm for the disease prediction and disease complication risk prediction as depicted in FIGS. 17 D-G. Various hyperparameters such as number of trees, maximum features, tree depth, loss criterion and the like are tuned for achieving best accuracy of the disease prediction and the disease complication risk prediction.

FIGS. 17 D-E are tabular representations depicting results 1700 D-E of the disease and health condition prediction, in accordance with an embodiment of the present disclosure. In this case, the results 1700 D-E of the disease and the health condition prediction are with respect to healthy (HLTY) and diabetes (DB) persons. Further, in this case, an accuracy of one hundred percentage is achieved for the disease prediction. FIGS. 17 F-G are tabular representations depicting results 1700 F-G of the disease complication risk prediction, in accordance with an embodiment of the present disclosure. In this case, the results 1700 F-G of the disease complication risk prediction are with respect to cardiovascular diseases (DB_C), hypertension (DB_H), hypertension and gastro diseases (DB_HG). Further, in this case, the accuracy of ninety-six percentage is achieved for the disease complication risk prediction.

FIG. 17 H is a graphical representation 1700 H depicting a process of predicting prakriti and generating a disease risk of the person, in accordance with an embodiment of the present disclosure. In this case, it is inferred that a disease risk level of the person based on the prakriti, symptoms and pulse is low.

FIG. 17 I is a pictorial representation 1700 I depicting various recommendations for alleviating the predicted disease and improving the health condition, in accordance with an embodiment of the present disclosure. The one or more recommendations includes increasing intake of cereals and meals, pulses, fruits, edible oils and practicing specific asanas of yoga. The recommendations to alleviate the disease may be based on the results of the disease prediction and the disease complication risk prediction.

Additionally, a network has an explainable artificial intelligence built into the conversational artificial intelligence-based adaptive questionnaire framework so that disease probabilities based on selected symptoms is also displayed which aids doctors in making diagnostic decisions. Additionally, the explainable artificial intelligence framework also assesses importance of each feature contributing to a vikriti decision. Severity of symptoms may also be asked through the adaptive questionnaire form. The disease prediction probability is presented as a percentage or a score. In future, causation-disease, causation-symptom networks may be used to precisely understand the causes of diseases or symptoms and to design a recommendation engine.

In an embodiment, the present invention has the following advantages. Currently, there are more than 4 lakh Ayurveda doctors practising Ayurveda who may potentially use the digital kiosk 100 in their practice. Additionally, more than fifteen thousand health and wellness centres are planned offering Ayurveda consultations. Further, the digital kiosk 100 also has application in foundations offering programs focused on health and wellness. Finally, the digital kiosk 100 may be deployed for corporate customers and in public places such as malls, train stations, airports and the like for health and wellness assessments.

The present invention targets evidence-based Ayurveda and other traditional medicine systems such as traditional Chinese medicine, Siddha, Unani, and the like, which may help greater than hundred million people in personalized health, wellness, and integrative medicine. This is achieved by leveraging ayurveda principles and using digital biomarkers, biochemical and genomics markers. Finally, the machine and deep learning algorithms are used for processing these multi-modal datasets to deliver highly personalized Ayurveda. This integrated approach may significantly help in mainstreaming Ayurveda and other traditional medicine systems such as the traditional Chinese medicine. Finally, the personalized and preventive nature of the traditional medicine systems may help in reducing global health care costs and reduce deaths due to chronic diseases and may improve nation's productivity through traditional medicine system-based health and wellness interventions. The present invention provides accurate Ayurveda disease diagnosis including sub-types. The present invention provides fast and personalized prakriti and vikriti estimation. The present invention provides continuous and remote feedback on multiple visits. The present invention provides various personalized and holistic interventions such as medicines, diet, and the like. The digital kiosk 100 is integrated with one or more health sensors 102, computer vision and AI for quantifiable traditional medicine parameter estimation. The present invention provides various objective decisions. The present invention utilizes computer vision based prakriti determination. The present invention provides exact ayurveda disease diagnosis including disease sub-types.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments herein can comprise hardware and software elements.

The embodiments that are implemented in software include but are not limited to, firmware, resident software, microcode, etc. The functions performed by various subsystems described herein may be implemented in other subsystems or combinations of other subsystems. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

Input/output (I/O) devices (as shown in FIG. 1) (including but not limited to keyboards, displays, pointing devices, various physiological sensors, electronic and optical sensors and the like) can be coupled to the system either directly or through intervening U/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random-access memory (RAM), read-only memory (ROM), and an input/output (I/O) adapter. The I/O adapter can connect to peripheral devices, such as disk units and tape drives, or other program storage devices that are readable by the system. In addition, the system may also comprise of Graphical Processing Unit (GPU) or Tensor Processing Unit (TPU) for running machine and (or) deep learning algorithms. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

A description of an embodiment with several components in communication with each other does not imply that all such components are required. On the contrary, a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article, or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

I claim:

1. A digital kiosk (100) for performing integrative analysis of a health and disease condition of a patient using Artificial Intelligence (AI) based traditional data and modern data network, the digital kiosk (100) comprising:
a three-dimensional image capturing system configured for capturing phenotypic features associated with the patient using one or more computer vision-based models;
one or more digital health sensors (102) configured for capturing physiological health signals associated with the patient;
a user interface for obtaining one or more user inputs from the patient;
a communication module for establishing a communication session with one or more external devices (106);
a hardware processor (208); and
a memory (202) coupled to the hardware processor (208), wherein the memory (202) comprises a set of program instructions, that when executed by the hardware processor (208) causes the hardware processor (208) to:
collect patient information and the phenotypic features associated with the patient from a plurality of medical devices, the computer vision-based models, and a conversational artificial intelligence-based adaptive questionnaire, and one or more inputs from digital biomarkers and modern markers comprising biochemical markers, clinical markers, genomic markers, and multi-omics markers, wherein the phenotypic features comprise anatomic features, physical features, physiological features, and psychological features of the patient; and
collect blood pulse parameters from the captured physiological health signals for traditional medicine diagnosis from the one or more health sensors (102), wherein the traditional medicine comprises at least one of: Ayurveda, traditional Chinese medicine, siddha, and unani, and wherein the blood pulse parameters comprise at least one of: pulse rate, pulse rate variability, pulse pressure, pulse transit time, and pulse morphology;
apply the collected patient information, the captured phenotypic features, the one or more inputs and the blood pulse parameters associated with the patient on to a trained machine learning model; and
predict a real time set of traditional medicine system parameters based on the results of the trained machine learning model;
compare the real time set of traditional medicine system parameters with a pre-stored real time set of traditional medicine system parameters;
identify a disease based on the compared results and based on a pre-stored disease database;
generate a recommendation message to the patient based on the identified disease, wherein the recommendation message comprises of a health and disease condition of the patient, health parameters, therapeutic interventions, clinical interventions, one or more medical remedies, and a treatment plan;
perform one or more operations based on the generated recommendation message and a patient prior approval, wherein the one or more operations comprises generating alerts for the patient representatives, generating alerts for medical representatives, generating a new treatment plan and generating a new diet plan;
output the generated recommendation message and the one or more operations on the user interface; and
update the trained machine learning model based on the predicted real time set of traditional medicine system parameters and actual patient outcomes.

2. The digital kiosk (100) as claimed in claim 1, wherein the one or more health sensors (102) comprises a magnetic sensor (124), a PPG sensor (118), an ECG sensor (114), an EEG sensor (116), a temperature sensor (120), and a weight sensor (122).

3. The digital kiosk (100) as claimed in claim 1, wherein to predict the real time set of traditional medicine system parameters based on the results of the trained machine learning model, the hardware processor (208) is configured to estimate dosha imbalance and dhatus effected.

4. The digital kiosk (100) as claimed in claim 1, wherein to estimate the real time set of traditional Chinese medicine system parameters based on the results of the of the trained machine learning model, the hardware processor (208) is configured to estimate baseline cun, guan and chi and imbalance in cun, guan and chi.

5. The digital kiosk (100) as claimed in claim 1, wherein the phenotypic feature comprises digital markers extracted from pulse electrocardiogram (ECG) data, photo plethysmograph (PPG) data, electroencephalogram (EEG) data, bioimpedance sensor data, galvanic skin response data, multispectral reflectance data, transmittance data, autofluorescence data from a plurality of body parts, sleep activity data, physical activity data and mental activity data.

6. The digital kiosk (100) as claimed in claim 1, wherein, in predicting the real time set of traditional medicine system parameters based on the results of the trained machine learning model, the hardware processor (208) is configured to:
dynamically map each of the patient information with the captured phenotypic features, the one or more inputs and the blood pulse parameters associated with the patient;
validating each of the patient information, the captured phenotypic features, the one or more inputs and the blood pulse parameters based on rules of the trained machine learning model;
generating a confidence score for each of the captured phenotypic features, the one or more inputs and the blood pulse parameters based on results of validation; and
predicting the real time set of traditional medicine system parameters based on the generated confidence score.

7. The digital kiosk (100) as claimed in claim 1, wherein the traditional medicine system parameters comprise prakriti level and vikriti level.

8. The digital kiosk (100) as claimed in claim 1, wherein the three-dimensional image capturing system is further configured to capture one or more images of the patient, pre-process the one or more images to extract the phenotypic features of the patient using the computer vision-based models; and transmit the extracted phenotypic features to the hardware processor (208).

9. The digital kiosk (100) as claimed in claim 1, wherein the user interface is further configured to display the conversational artificial intelligence-based adaptive questionnaire to the patient and receive one or more responses to the conversational artificial intelligence-based adaptive questionnaire from the patient, wherein the conversational artificial intelligence-based adaptive questionnaire is generated at real-time based on the patient information.

10. The digital kiosk (100) as claimed in claim 1, wherein the communication module is further configured to transmit the one or more operations to the one or more external devices (106) and receive responses to the transmitted one or more operations from the one or more external devices (106).

11. The digital kiosk (100) as claimed in claim 1, the hardware processor (208) is configured to print the recommendation message and responses from one or more doctors.

12. A method (300) for performing integrative analysis of a health and disease condition of a patient using Artificial Intelligence (AI) based traditional data network, the method (300) comprises:
capturing, by a three-dimensional image capturing system, phenotypic features associated with the patient using one or more computer vision-based models;
capturing, by one or more health sensors (102), physiological health signals associated with the patient;
collecting, by a hardware processor, a patient information and the phenotypic features associated with the patient from a plurality of medical devices, the computer vision-based models, and a conversational artificial intelligence-based adaptive questionnaire, and one or more inputs from digital biomarkers and modern markers comprising clinical markers, biochemical markers, genomic markers, and multi-omics markers, wherein the phenotypic features comprise anatomic features, physical features, physiological features, and psychological features of the patient;
collecting, by the hardware processor, blood pulse parameters from the captured physiological health signals for traditional medicine diagnosis from one or more health sensors (102), wherein the traditional medicine includes at least one of: Ayurveda, traditional Chinese medicine, siddha, and unani, and wherein the blood pulse parameters includes at least one of: pulse rate, pulse rate variability, pulse pressure, pulse transit time, and pulse morphology;
applying, by the hardware processor, the collected patient information, the captured phenotypic features, the one or more inputs and the blood pulse parameters associated with the patient on to a trained machine learning model;
predicting, by the hardware processor, a real time set of traditional medicine system parameters based on the results of the trained machine learning model;
comparing, by the hardware processor, the real time set of traditional medicine system parameters with a pre-stored real time set of traditional medicine system parameters;
identifying, by the hardware processor, a disease based on the compared results and based on a pre-stored disease database;
generating, by the hardware processor, a recommendation message to the patient based on the identified disease, wherein the recommendation message comprises of a health and disease condition of the patient, health parameters, therapeutic interventions, clinical interventions, one or more medical remedies, and a treatment plan;
performing, by the hardware processor, one or more operations based on the generated recommendation message and a patient prior approval, wherein the one or more operations comprises generating alerts for the patient representatives, generating alerts for medical representatives, generating a new treatment plan and generating a new diet plan;
outputting, by the hardware processor, the generated recommendation message and the one or more operations on the user interface; and
updating, by the hardware processor, the trained machine learning model based on the predicted real time set of traditional medicine system parameters and actual patient outcomes.

13. The method (300) as claimed in claim 12, wherein predicting the real time set of traditional medicine system parameters based on the results of the trained machine learning model, comprises:
dynamically mapping each of the patient information with the captured phenotypic features, the one or more inputs and the blood pulse parameters associated with the patient;
validating each of the patient information, the captured phenotypic features, the one or more inputs and the blood pulse parameters based on rules of the trained machine learning model;

generating a confidence score for each of the captured phenotypic features, the one or more inputs and the blood pulse parameters based on results of validation; and predicting the real time set of traditional medicine system parameters based on the generated confidence score.

14. The method (300) as claimed in claim 12, further comprising:

capturing one or more images of the patient, pre-processing the one or more images to extract the phenotypic features of the patient using the computer vision-based models; and transmitting the extracted phenotypic features to the hardware processor.

15. The method (300) as claimed in claim 12, further comprising:

displaying the conversational artificial intelligence-based adaptive questionnaire to the patient; and receiving one or more responses to the conversational artificial intelligence-based adaptive questionnaire from the patient, wherein the conversational artificial intelligence-based adaptive questionnaire is generated at real-time based on the patient information.

\* \* \* \* \*